(12) United States Patent
Mizutani et al.

(10) Patent No.: US 7,678,368 B2
(45) Date of Patent: Mar. 16, 2010

(54) FUCOIDAN-CONTAINING COSMETICS

(75) Inventors: Shigetoshi Mizutani, Shiga (JP); Suzu Deguchi, Otsu (JP); Eiji Kobayashi, Otsu (JP); Eiji Nishiyama, Moriyama (JP); Hiroaki Sagawa, Kusatsu (JP); Ikunoshin Kato, Uji (JP)

(73) Assignee: Takara Bio Inc., Otsu-shi (JP)

( * ) Notice: Subject to any disclaimer, the term of this patent is extended or adjusted under 35 U.S.C. 154(b) by 1046 days.

(21) Appl. No.: 11/311,341

(22) Filed: Dec. 20, 2005

(65) Prior Publication Data

US 2006/0093566 A1 May 4, 2006

Related U.S. Application Data

(62) Division of application No. 10/148,486, filed as application No. PCT/JP00/08412 on Nov. 29, 2000, now abandoned.

(30) Foreign Application Priority Data

| Nov. 30, 1999 | (JP) | ................... 11-341401 |
| Dec. 27, 1999 | (JP) | ................... 11-370004 |
| Mar. 23, 2000 | (JP) | ................... 2000-82738 |
| Jul. 21, 2000 | (JP) | ................... 2000-220374 |
| Oct. 5, 2000 | (JP) | ................... 2000-306772 |

(51) Int. Cl.
*A61K 8/73* (2006.01)
*A61P 17/14* (2006.01)

(52) U.S. Cl. ............... 424/70.13; 424/401; 424/725; 514/54; 514/880; 536/123; 536/123.1; 536/128

(58) Field of Classification Search ............ 514/54; 424/401, 725; 536/123, 123.1, 128; 426/658
See application file for complete search history.

(56) References Cited

U.S. PATENT DOCUMENTS

| 5,089,481 A | 2/1992 | Muto et al. |
| 5,618,798 A | 4/1997 | Bar-Shalom et al. |
| 5,650,137 A | 7/1997 | Nguyen et al. |
| 6,573,250 B2 | 6/2003 | Umeda et al. |

FOREIGN PATENT DOCUMENTS

| CN | 1382055 A | 11/2002 |
| EP | 0 916 269 A1 | 5/1999 |
| EP | 1 175 907 A1 | 1/2002 |
| EP | 1226826 A1 | 7/2002 |
| JP | 64-31707 A | 2/1989 |
| JP | 64-85905 A | 3/1989 |
| JP | 1-305011 A | 12/1989 |
| JP | 10-165114 A | 6/1998 |
| JP | 10-176192 A | 6/1998 |
| JP | 10-245334 A | 9/1998 |
| JP | 11-1437 A | 1/1999 |
| JP | 11-21247 A | 1/1999 |
| JP | 11-130636 A | 5/1999 |
| JP | 2000-169322 A | 6/2000 |
| JP | 2000-351790 A | 12/2000 |
| JP | 2000-351801 A | 12/2000 |
| WO | WO-90/12561 A1 | 11/1990 |
| WO | WO-99/01478 A | 1/1999 |
| WO | WO-00/62785 A | 10/2000 |

OTHER PUBLICATIONS

Computer generated translation of JP 10-245334 published Sep. 14, 1998.

*Primary Examiner*—Sreeni Padmanabhan
*Assistant Examiner*—Sahar Javanmard
(74) *Attorney, Agent, or Firm*—Birch, Stewart, Kolasch & Birch, LLP

(57) ABSTRACT

To find a substance which has a skin cosmeticizing effect such as prevention of skin aging, amelioriation of sensitive skin, or antipruritic action, and can serve as an effective ingredient for a hair-care product, thereby providing cosmetics comprising the effective ingredient. Concretely, there are provided cosmetics characterized in that the cosmetics comprise as an effective ingredient a compound selected from a fucoidan, a degradation product thereof, a sulfated monosaccharide or a salt thereof.

4 Claims, 1 Drawing Sheet

FUCOIDAN-CONTAINING COSMETICS

CROSS-REFERENCE TO RELATED APPLICATIONS

The present application is a 37 C.F.R. §1.53(b) divisional of U.S. application Ser. No. 10/148,486 filed on May 30, 2002, now abandoned which is the National Phase of PCT International Application No. PCT/JP00/08412, filed Nov. 29, 2000, which in turn claims priority on Japanese Application Nos. 11-341401 filed Nov. 30, 1999, 11-37004 filed Dec. 27, 1999, 2000-82738 filed Mar. 23, 2000, 2000-220374 filed Jul. 21, 2000, and 2000-306772 filed Oct. 5, 2000. The entire contents of each of these applications is hereby incorporated by reference.

TECHNICAL FIELD

The present invention relates to use of an acidic saccharide compound for cosmetics.

BACKGROUND ART

Conventionally, blotches, freckles and wrinkles have been problems on cosmeticizing of skin. Recently, a large number of cosmetics preventing them have been know, and retinoic acid, α-hydroxy acid, retinol or the like has been reported as an effective ingredient thereof. However, these effective ingredients have some problems in skin irritability, stability and the like, and their effects cannot hardly be said to be satisfactory.

On the other hand, a hair-care product is a product which accelerates or stimulates growth of hair, used for the purposes of supplementing loss of hair by restoring hair, thereby inhibiting the reduction in the absolute number of hair. Generally, as the causations for hair loss, there are considered various factors such as activation of androgenic hormones in organs such as hair roots and sebaceous glands, lowering in blood flow rate into hair follicles, hypersecretion of sebum, abnormality of scalp due to generation of peroxides, oligotrophia and stresses. Generally, conventional hair-care products are formulated with a substance which eliminates or alleviates a factor to be considered as a causation for hair loss. For instance, there are formulated in a hair care product vitamins such as vitamin B and vitamin E, amino acids such as serine and methionine, vasodilators such as Lithospermi Radix extract and acetylcholine derivatives, anti-flammatory agents such as lithospermum root extract and hinokitiol, female hormone agents such as estradiol, skin hyperergasia agents such as cephalanthin, and these hair-care products have been used for prophylaxis and treatment of hair loss.

However, although various attempts have been made as described above, the conventional hair-care products had weaker prophylactic action for hair loss and weaker trichogenous action, so that satisfactory hair restoring effects could not be necessarily obtained.

A main object of the present invention is to find a substance which has a skin cosmeticizing effect such as prevention of skin aging, amelioration of sensitive skin, or antipruritic action, and can serve as an effective ingredient for a hair-care product, thereby providing cosmetics comprising the effective ingredient.

DISCLOSURE OF INVENTION

Summarizing the present invention, the present invention relates to cosmetics, characterized in that the cosmetics comprise a compound selected from a fucoidan, a degradation product thereof, a sulfated monosaccharide or a salt thereof as an effective ingredient. In addition, the present invention relates to use of a compound selected from a fucoidan, a degradation product thereof, a sulfated monosaccharide or a salt thereof for manufacturing cosmetics.

The fucoidan used in the present invention is not particularly limited, as long as the fucoidan is capable of exhibiting skin cosmeticizing effects (for instance, those caused by action for prevention of skin aging, action for amelioration of sensitive skin, antipruritic action, and the like) and/or hair restoring effects (for instance, those caused by trichogenic action, hair growing action, hair nourishing action, action for preventing hair loss and the like). As the fucoidan, there can be preferably used fucoidans derived from algae and fucoidans derived from Echinodermata. As the fucoidan used in the present invention, those fucoidans having definite structures are preferable, and it is preferable to use fucoidans selected from U-fucoidan, F-fucoidan and G-fucoidan derived from *Kjellmaniella crassifolia*, and a fucoidan derived from *Cladosiphon okamuranus*, comprising each of sulfated saccharides represented by the following general formulas (I) to (IV) as the essential component of constituent saccharide.

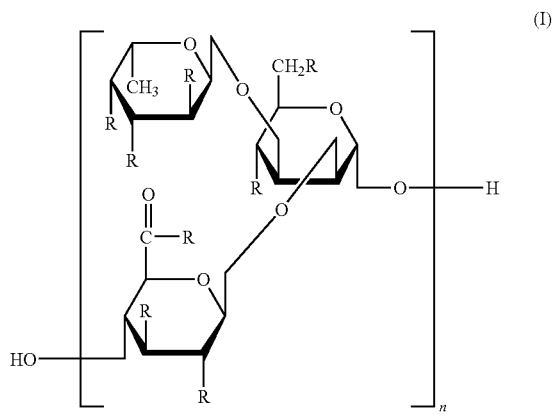

wherein R is OH or OSO$_3$H, and n is an integer of 1 or more;

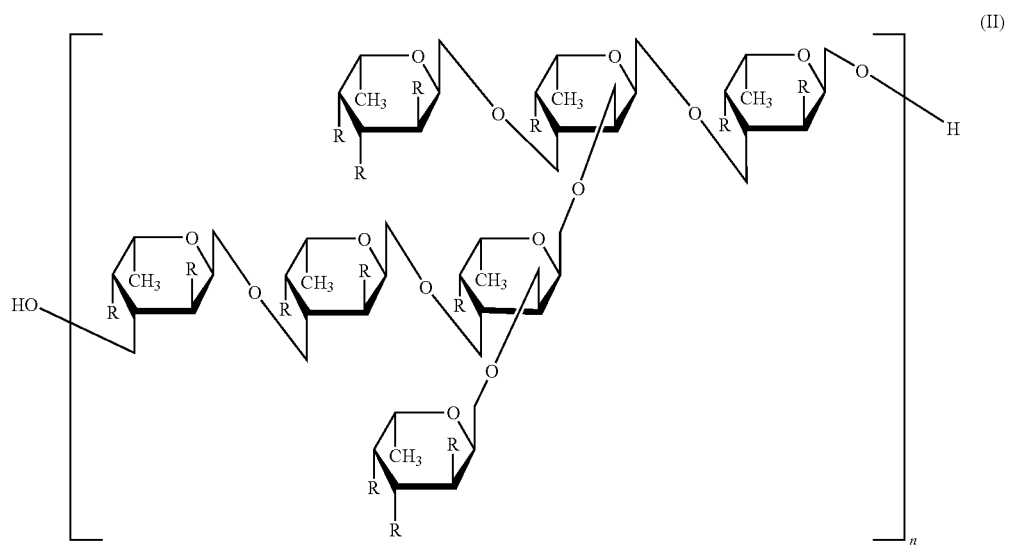
wherein R is OH or OSO$_3$H, and n is an integer of 1 or more;
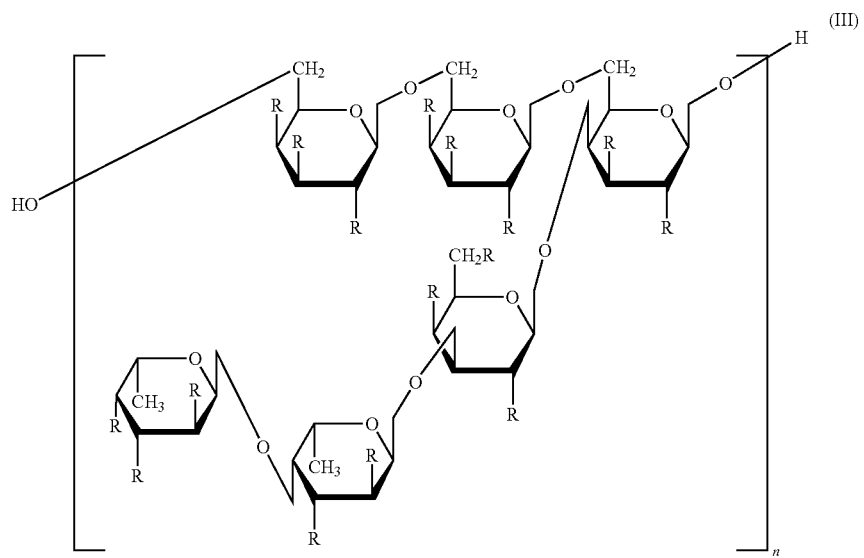
wherein R is OH or OSO$_3$H, and n is an integer of 1 or more; and

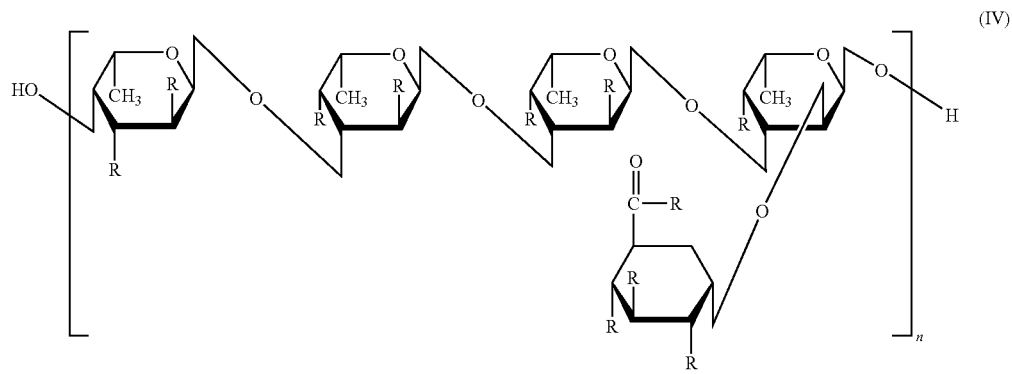

(IV)

wherein R is OH or OSO$_3$H, and n is an integer of 1 or more.

In addition, the fucoidan is preferably a non-stringy fucoidan, from the viewpoints of the non-precipitating property, the solubility in a base material for cosmetics, and the like.

As the degradation product of the fucoidan, there can be used, for instance, acid degradation products of fucoidans, and enzyme degradation products of fucoidans. The acid degradation products of fucoidans and the enzyme degradation products of fucoidans used in the present invention may be any of those which exhibit skin cosmeticizing action and/or hair restoring action, and can be prepared by using these actions as indices. In the present invention, a compound selected from the compound represented by the following formula (V), the compound represented by the following formula (VI), and the compound represented by the following formula (VII) can be preferably used.

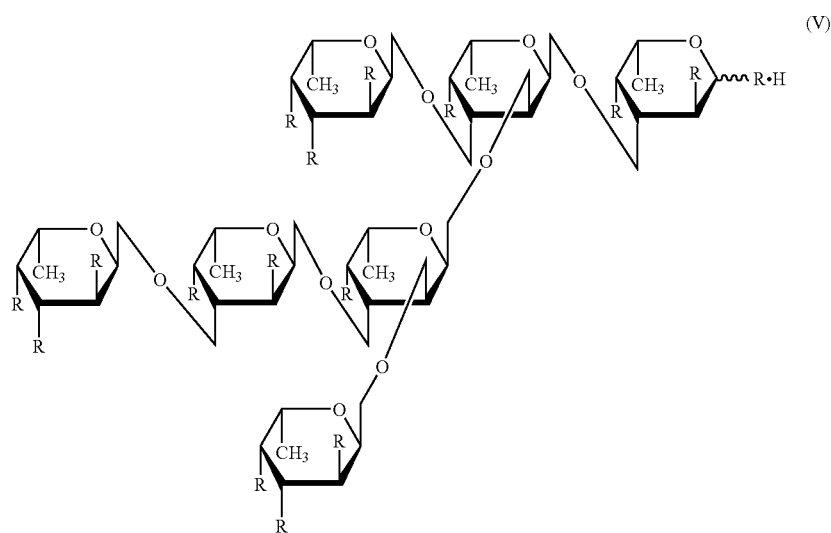

(V)

wherein R is OH or OSO$_3$H;

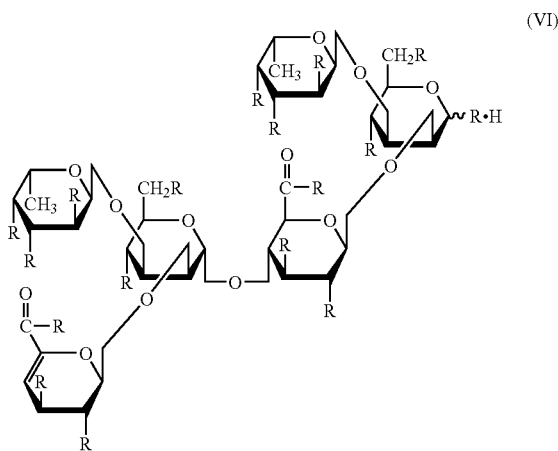

wherein R is OH or OSO$_3$H; and

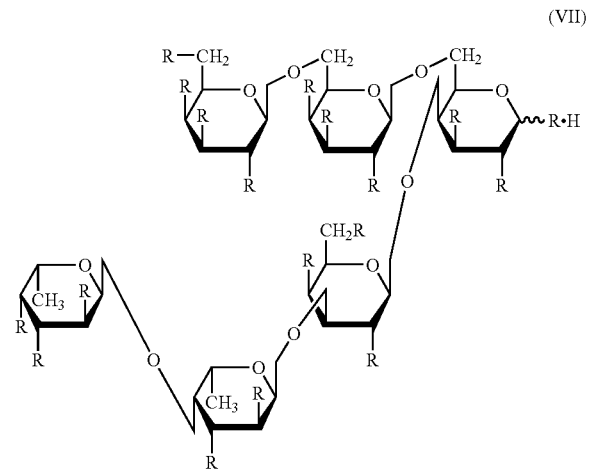

wherein R is OH or OSO$_3$H.

The forms of the cosmetics of the present invention are exemplified by a lotion, a milky lotion, cream, a facial pack, an ointment, a bathing agent, a bath detergent, a facial cleansing agent, a hair lotion, a hair-care product, or a shampoo agent. In addition, the present invention can be provided in the form of a medicament, a quasi drug, a food, a beverage, or the like.

The cosmetics of the present invention can be used as cosmetics for prevention of aging, amelioration of sensitive skin, antipruritus, amelioration of allergy, amelioration of atopic diseases and the like.

In addition, as the cosmetics of the present invention, there are provided a hair-care product having excellent hair restoring action, comprising a compound selected from a fucoidan, a degradation product thereof, a sulfated monosaccharide or a salt thereof as an effective ingredient; and a hair-care product further comprising a component capable of synergistically enhancing the hair restoring action (hair restoring action-enhancing component) when the component is used together with the compound selected from a fucoidan, a degradation product thereof, a sulfated monosaccharide or a salt thereof. In addition, the cosmetics and the hair-care product can be provided as foods or beverages. Here, the preferred hair restoring action-enhancing component is exemplified by minoxidil and calpronium chloride.

BEST MODE FOR CARRYING OUT THE INVENTION

Figure 1:
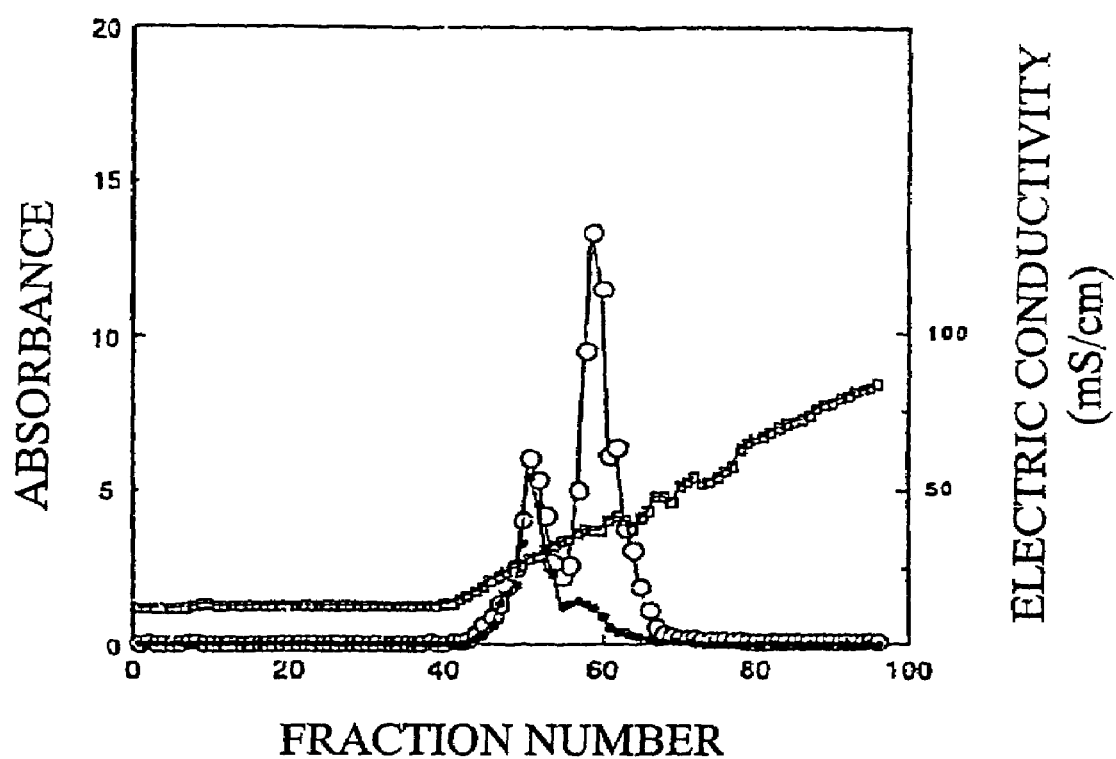
FIG. 1 is a graph showing an elution pattern of the fucoidan derived from *Kjellmaniella crassifolia* on DEAE-Cellulofine A-800 column.

One of the great features of the cosmetics of the present invention resides in that the cosmetics comprise as an effective ingredient a compound selected from a fucoidan, a degradation product thereof, a sulfated monosaccharide and a salt thereof, which especially have physiological actions such as skin cosmeticizing action and/or hair restoring action. The phrase "selected from" as referred to herein means that one or more compounds are selected.

The term "skin cosmeticizing action" used herein refers to action for prevention of skin aging, action for amelioration of sensitive skin, antipruritic action, and the like, and effects exhibited by these actions are referred to as "skin cosmeticizing effects." Here, the term "action for prevention of skin aging" means an action for suppressing skin aging, such as giving the skin moistness and smoothness, thereby reducing dryness, blotches and the like. The skin cosmeticizing action can be evaluated, for instance, by the methods described in items (8) to (10) of Example 13. The desired skin cosmeticizing action can be exhibited by the compound selected from a fucoidan, a degradation product thereof, a sulfated monosaccharide and a salt thereof, which are capable of exhibiting excellent effects at least for the evaluation items described in items (8) to (10) of Example 13.

In addition, the term "hair restoring action" refers to trichogenous action, hair growing action, hair nourishing action, action for preventing hair loss, and the like, effects exhibited by these actions are referred to as "hair restoring effects." The hair restoring action can be evaluated, for instance, by the methods described in Examples 13 to 20. A compound selected from a fucoidan, a degradation product thereof, a sulfated monosaccharide and a salt thereof, which have the action, can exhibit a hair restoring effect.

The fucoidan and a degradation product thereof used in the present invention are not particularly limited, as long as the fucoidan and a degradation product thereof have skin cosmeticizing action and/or hair restoring action. For instance, there can be used a fucoidan derived from an algae. In the present invention, the fucoidan is a generic term for a polysaccharide comprising sulfated fucose as a constituting saccharide. In other words, in the present invention, there can be used a sulfated fucose-containing polysaccharide and/or a degradation product thereof.

The sulfated fucose-containing polysaccharide is exemplified by sulfated fucan, sulfated fucogalactan, sulfated fucoglucuronomannan, sulfated glucuronoxylofucane, sulfated xylofucoglucuronan, sulfated ascorfilan, sulfated glucuronogalactofucane, sulfated glucuronofucane, and the like.

These fucoidans may be each prepared by a known method, and the resulting purified products, fucoidan-containing products or the like can be used in the present invention.

For instance, marine algae of *Laminariales, Chordariales, Fucales*, and the like, such as *Kjellmaniella crassifolia, Laminaria japonica, Kjellmaniella, Fucus, Nemacystus, Cladosiphon okamuranus, Undaria, Undaria pinnatifida* (Wakame Mekabu), *Ecklonia kurome, Eisenia, Ecklonia*, Giant kelp, *Lessonia nigrescence* and *Ascophyllum nodosum* richly contain fucoidans especially suitable for the use in the present invention. This is why they are preferable as the raw material. Here, sulfated polysaccharides derived from Rhodophyceae, for instance, sulfated polysaccharides derived from *Gelidiun amansii, Gracilaria*, and *Pteroclavia capillacae* have the same effects as those of the fucoidan used in the present invention, and can be also used in the present invention.

The fucoidan used in the present invention is exemplified by the fucoidans derived from the algae mentioned above, and the fucoidan is not particularly limited, as long as the fucoidan is a polysaccharide comprising a sulfated fucose as a constituent, wherein the polysaccharide has skin cosmeticizing action and/or hair restoring action. There may be used fucoidans derived from Echinodermata, for instance, sea cucumber, Echnoidea, Asterozoa, and the like.

For instance, a fucoidan is prepared from *Kjellmaniella crassifolia*, and the resulting fucoidan can be separated into glucuronic acid-containing fucoidan having a sulfated saccharide repeating structure represented by the general formula (I) ("U-fucoidan" mentioned above) and glucuronic acid non-containing fucoidan having a sulfated saccharide repeating structure represented by the general formula (II) ("F-fucoidan" mentioned above). Each of the fucoidans can be used as an effective ingredient of the present invention. Also, sulfated fucogalactan having a sulfated saccharide repeating structure represented by the general formula (III) ("G-fucoidan" mentioned above) can be prepared from *Kjellmaniella crassifolia* and suitably used.

In addition, a fucoidan having a sulfated saccharide repeating structure represented by the general formula (IV) can be prepared from *Cladosiphon okamuranus*, and suitably used.

After the preparation of the fucoidans from *Kjellmaniella crassifolia* according to known methods, U-fucoidan and F-fucoidan are separated by using an anionic exchange resin, a surfactant or the like. The existing ratio of U-fucoidan to F-fucoidan derived from *Kjellmaniella crassifolia* is about 1:2 in a weight ratio. U-fucoidan contains fucose, mannose, galactose, glucuronic acid and the like, and its sulfate content is about 20% by weight. F-fucoidan contains fucose as its main component, and its sulfate content is about 50% by weight. The molecular weight for both substances is distributed, centering about 200000 (*Summary of 18th Sugar Symposium*, p. 159, 1996).

U-fucoidan and F-fucoidan can be separated, for instance, by applying a fucoidan solution prepared from *Kjellmaniella crassifolia* onto DEAE-Cellulofine A-800 column, and carrying out elution by the concentration gradient technique using NaCl-containing buffer. One of the examples is shown in FIG. 1. Concretely, FIG. 1 is a diagram showing the separation of U-fucoidan and F-fucoidan, wherein the former peak in the FIGURE is U-fucoidan, and the latter peak is F-fucoidan.

In addition, for instance, each of the fucoidan derived from *Fucus*, the fucoidan derived from *Nemacystus*, the fucoidan derived from *Cladosiphon okamuranus*, the fucoidan derived from *Undaria*, the fucoidan derived from *Undaria pinnatifida*, the sulfated polysaccharide derived from *Gelidium amansii*, the sulfated polysaccharide derived from *Gracilaria*, the fucoidan derived from *Lessonia*, the fucoidan derived from *Ascophyllum*, the sulfated polysaccharide derived from *Pteroclavia capillacae*, and the fucoidan derived from other algae can be also prepared by a known method, and used in the present invention.

The fucoidan derived from Echinodermata suitably used in the present invention includes, for instance, the fucoidan contained in sea cucumber disclosed in Japanese Patent Laid-Open No. Hei 4-91027, and the fucoidan can be prepared from sea cucumber by the method described in the publication.

In addition, the degradation products of the fucoidans having skin cosmeticizing action and/or hair restoring action can be prepared by a known method such as an enzymological method, a chemical method, or a physical method, and a desired degradation product having skin cosmeticizing action and/or hair restoring action can be selected and used.

The preferable preparation method for the degradation product of the fucoidan used in the present invention is acid degradation method and enzyme degradation method. The degradation product having skin cosmeticizing action and/or hair restoring action can be prepared by subjecting the fucoidan to an acid degradation or an enzyme degradation.

The conditions for the acid degradation of the fucoidan used in the present invention are not particularly limited, as long as the conditions enable to generate the degradation product having skin cosmeticizing action and/or hair restoring action (hereinafter referred to as "degradation product of the present invention"). The conditions can be determined by evaluating the physiological actions of the resulting degradation product.

For instance, the fucoidan is dissolved or suspended in an acid and subjected to the reaction, thereby generating a degradation product of the present invention. Also, the reaction mixture may be heated during the reaction, thereby shortening the time period required for the generation of the degradation product of the present invention.

The kinds of the acids for dissolving or suspending the fucoidan are not particularly limited. There can be used inorganic acids such as hydrochloric acid, sulfuric acid and nitric acid; organic acids such as citric acid, formic acid, acetic acid, lactic acid and ascorbic acid; and solid acids such as cationic exchange resin, cationic exchange fiber and cationic exchange membrane.

The concentration of the acid is not particularly limited, and the acid can be used at a concentration of preferably from 0.0001 to 5 N or so, more preferably from 0.01 to 1 N or so. In addition, the reaction temperature is not particularly limited, and the reaction temperature may be set at preferably from 0° to 200° C., more preferably from 20° to 130° C.

In addition, the reaction time is not particularly limited, and the reaction time may be set at preferably from several seconds to several days. The kinds and the concentration of the acids, the reaction temperature, and the reaction time may be properly selected depending upon the generated amount of the degradation product of the present invention and the degree of polymerization of the degradation product. For instance, during the preparation of the degradation product of the fucoidan, the organic acid such as citric acid, lactic acid or malic acid is used, and the concentration of the acid is properly selected from the range of several dozens mM to several M, the heating temperature from the range of 50° to 110° C., preferably 70° to 95° C., and the heating time from the range of several minutes to 24 hours, whereby the degradation product of the present invention can be prepared. The acid degradation product of the fucoidan is exemplified by the acid degradation product of the fucoidan derived from *Kjellmaniella crassifolia*, and this degradation product can be used as dietary fiber especially having new physiological function of strong skin cosmeticizing action and/or hair restoring action.

The degradation product of the present invention can be fractionated by using its skin cosmeticizing action and/or hair restoring action as an index. For instance, an acid degradation product can be fractionated based on a molecular weight by means of a fractionation method such as gel filtration method, molecular weight fractionation membrane, or the like.

As an example of gel filtration method, Cellulofine GCL-300 can be used to prepare any molecular weight fractions, for instance, one having a molecular weight exceeding 25000, one having a molecular weight of 25000 to exceeding 10000, one having a molecular weight of 10000 to exceeding 5000, one having a molecular weight of 5000 or less. Cellulofine GCL-25 can be used to prepare any molecular weight fractions, for instance, one having a molecular weight of 5000 or less, one having a molecular weight of 5000 to exceeding 3000, one having a molecular weight of 3000 to exceeding 2000, one having a molecular weight of 2000 to exceeding 1000, one having a molecular weight of 1000 to exceeding 500, one having a molecular weight of 500 or less.

In addition, the molecular weight fractionation can be industrially carried out by using an ultrafiltration membrane. For instance, a fraction having a molecular weight of 30000 or less can be prepared by using FE10-FUS0382 manufactured by DAICEL CHEMICAL INDUSTRIES, LTD., and a fraction having a molecular weight of 6000 or less can be prepared by using FE-FUS-T653 manufactured by the same. Further, a fraction having a molecular weight of 500 or less can be obtained by using a nanofilter membrane. Any molecular weight fractions can be prepared by combining these gel filtration method and molecular weight fractionation method. For instance, in the degradation product of the fucoidan derived from *Fucus*, a fraction having a molecular weight of 30000 or more exhibits a strong skin cosmeticizing action and/or hair restoring action, so that the use of the fucoidan derived from *Fucus* having a molecular weight of 30000 or more is suitable in the present invention.

The degradation product of the fucoidan having the skin cosmeticizing action and/or hair restoring action which can be used in the present invention is exemplified by the compound represented by the formula (V), the compound represented by the formula (VI) and the compound represented by the formula (VII), and each of these compounds can be prepared, for instance, in accordance with the method disclosed in WO 99/41288, WO 96/34004 and International Application No. PCI/JP 00/00965. The oligosaccharide having a repeating structure of the compound represented by the formula (V) as a basic backbone structure or the oligosaccharide having a repeating structure of the compound represented by the formula (VI) as a basic backbone structure can be each used in the present invention. Further, the oligosaccharide having a repeating structure of the compound represented by the formula (VII) as a basic backbone structure can be also used in the present invention. In addition, as the degradation product of the present invention, there are exemplified those degradation products of the fucoidans described in WO 99/41288, WO 96/34004 and International Application No. PCT/JP 00/00965.

The compound represented by the formula (V) can be obtained by treating the previously mentioned F-fucoidan with endo-sulfated polysaccharide degrading enzyme (F-fucoidan degradation enzyme) produced by *Alteromonas* sp. SN-1009 (FERM BP-5747), and purifying the degradation product. As to the content and the site of sulfate group in the compound, any ones can be purified from the degradation product. In addition, the polymer of the compound represented by the formula (V) is contained in the degradation product, and can be separated and purified depending on its purposes.

The compound represented by the formula (VI) can be obtained by treating the previously mentioned U-fucoidan with endo-sulfated polysaccharide degrading enzyme (U-fucoidan degradation enzyme) produced by *Flavobacterium* sp. SA-0082 (FERM BP-5402), and purifying the degradation product. As to the content and the site of sulfate group in the compound, any ones can be purified from the degradation product. In addition, the polymer comprising the compound represented by the formula (VI) as a basic backbone structure is also contained in the degradation product, and can be separated and purified depending on its purposes.

In addition, the previously mentioned G-fucoidan can be obtained by degrading the fucoidan derived from *Kjellmaniella crassifolia* with F-fucoidan degradation enzyme produced by *Alteromonas* sp. SN-1009 (FERM BP-5747), and U-fucoidan degradation enzyme produced by *Flavobacterium* sp. SA-0082 (FERM BP-5402), and purifying the degradation product.

*Flavobacterium* sp. SA-0082 (FERM BP-5402) also produces endo-sulfated polysaccharide degrading enzyme (G-fucoidan degradation enzyme). A degradation product of G-fucoidan can be prepared by treating G-fucoidan with G-fucoidan degradation enzyme, and the product can be purified as occasion demands. The compound represented by the formula (VII) is one such example. As to the content and the site of sulfate group in the compound, any ones can be purified from the degradation product. In addition, the polymer of which basic backbone structure comprises the compound represented by the formula (VII) is also contained in the degradation product, and can be separated and purified depending on its purposes.

An example of the compound represented by the formula (V) includes the compound represented by the formula (VIII) given below. In addition, an example of the compound represented by the formula (VI) includes the compound represented by the formula (X) given below. Further, an example of the compound represented by the formula (VII) includes the compound represented by the formula (IX) given below.

In addition, one unit (U) of the F-fucoidan degradation enzyme, the U-fucoidan degradation enzyme or the G-fucoidan degradation enzyme mentioned above is defined as an amount of enzyme for cleaving each of glycosyl bond of F-fucoidan, U-fucoidan or G-fucoidan in an amount equivalent to 1 μmol in one minute.

The salt of the fucoidan or the salt of the degradation product thereof can be prepared by a usual method from the fucoidan or the degradation product thereof. In addition, the degradation product of the fucoidan can be properly sulfated as desired for use, and the method for sulfation can be carried out in accordance with a known method.

The fucoidan, a degradation product thereof and a salt thereof, having skin cosmeticizing action and/or hair restoring action, which are used in the present invention, is useful as an effective ingredient for cosmetics such as a lotion, a milky lotion, cream, a facial pack, an ointment, a bathing agent, a bath detergent or a facial cleansing agent owing to its skin cosmeticizing action (action for preventing skin aging or the like). In addition, the fucoidan or the like is useful as an effective ingredient for cosmetics as hair-care products such as a hair lotion, a hair tonic, a hair nourishing agent, and a hair loss preventing agent owing to its hair restoring action. Therefore, the present invention provides cosmetics having excellent skin cosmeticizing action and/or hair restoring action, comprising as an effective ingredient one compound selected from a fucoidan, a degradation product thereof and a salt thereof, having skin cosmeticizing action and/or hair restoring action. The effective ingredient of the cosmetics is preferably, for instance, a compound selected from U-fucoidan, F-fucoidan, G-fucoidan, the fucoidan derived from *Cladosi-*

*phon okamuranus* and a degradation product thereof, and there can be provided bio-cosmetics comprising the compound as an effective ingredient. Here, as the degradation product of the fucoidan, there can be preferably used, for instance, a compound selected from the compounds represented by the formulas (V) to (VII).

The fucoidan is a polysaccharide comprising sulfated fucose. The present inventors have found that a sulfated monosaccharide also has skin cosmeticizing action and/or hair restoring action. In other words, the present inventors also provide cosmetics comprising a sulfated monosaccharide or a salt thereof as an effective ingredient.

The sulfated monosaccharide or a salt thereof used in the cosmetics is not particularly limited, as long as the sulfated monosaccharide or a salt thereof has skin cosmeticizing action and/or hair restoring action, and is exemplified by a sulfated fucose, a sulfated glucose, a sulfated galactose, a sulfated xylose, a sulfated 2-deoxy-glucose, a sulfated mannose, a sulfated talose and salts thereof.

These sulfated monosaccharides can be prepared by known synthesis methods. Alternatively, the sulfated monosaccharides may be prepared by degrading a sulfated polysaccharide in a natural product, and purifying the degradation product. In addition, the salt thereof can be prepared by a conventional method.

The content of the compound selected from the fucoidan, a degradation product thereof, the sulfated monosaccharide and a salt thereof in the cosmetics of the present invention is usually preferably from 0.0001 to 20% by weight, more preferably from 0.001 to 5% by weight, still more preferably from 0.03 to 3% by weight.

The cosmetics of the present invention can be prepared in accordance with a conventional method, and those usually used in cosmetics such as hydrocarbons, waxes, fats and oils, esters, higher fatty acids, higher alcohols, surfactants, perfume, pigments, anticorrosive agents, antioxidants, ultraviolet absorbents, alcohols, pH adjustment agents, various ingredients with medicinal effect can be properly selected and formulated. Here, there may be added as desired a component having skin cosmeticizing action other than the compound selected from the fucoidan, a degradation product thereof, the sulfated monosaccharide and a salt thereof, which is an effective ingredient for the cosmetics of the present invention, and a trichogenous component, a hair growing component, a hair nourishing component, a hair loss preventing component or the like, each having hair restoring action. The component having skin cosmeticizing action includes retinoic acid, α-hydroxy acid, retinol, glycerol, polyethylene glycol, potassium hydroxide, triethanolamine, and other saccharides, and the component having hair restoring action includes minoxidil, calpronium chloride, heparin analogs, glyceryl monolinolate, linoleic acid, various crude drug extracts, and the like.

As the fucoidan contained in the cosmetics of the present invention, a non-stringy fucoidan is more excellent than a stringy fucoidan from the viewpoints of the non-precipitating property, the solubility to a base material for cosmetics, and the like, and a non-stringy fucoidan is preferable.

The form of the cosmetics is not particularly limited, as long as the skin cosmeticizing action can be expected, and the form includes, for instance, a lotion, a milky lotion, cream, a facial pack, an ointment, a bathing agent, a bath detergent, a facial cleansing agent, a shampoo agent or the like.

In addition, the form of the cosmetics as the hair-care products is not particularly limited, as long as the action to the hair can be expected, and the form includes, for instance, a lotion, a milky lotion, cream, an ointment, a hair lotion, a hair tonic, a hair nourishing agent, a hair loss preventing agent or a shampoo agent.

The hair-care product as one embodiment of the cosmetics of the present invention may be applied or pasted to a site in need of restoring hair. Alternatively, the hair-care product of the present invention may be orally taken by forming it into a drinkable or edible form.

The use embodiment of the cosmetics of the present invention is not particularly limited. For instance, the use embodiment of the above-mentioned hair-care product may be such that several milliliters of the hair-care product, which contains the fucoidan, a degradation product thereof, the sulfated monosaccharide and/or a salt thereof in an amount of, for instance, 0.1 ng to 100 mg per one milliliter of the hair-care product, may be applied to a site in need of restoring hair, or pasted to the site in the form of a pack containing the same amount as above at least once a day.

When the cosmetics of the present invention are used from the viewpoint of expecting skin cosmeticizing action, the desired effects can be obtained by using them similarly to the use embodiment as the above-mentioned hair-care product.

The orally taken amount is not particularly limited, as long as it is an amount by which the fucoidan, a degradation product thereof, the sulfated monosaccharide and/or a salt thereof exhibits skin cosmeticizing action and/or hair restoring action. The orally taken amount per day is usually preferably from 0.1 mg to 10 g, more preferably from 2 mg to 5 g, still more preferably from 10 mg to 2 g.

Incidentally, conventionally, various techniques have been proposed for the hair-care products used for accelerating or maintaining the growth of hair, and have been actually used.

As conventional effective ingredient for the hair-care products, there have been known minoxidil (Japanese Patent Laid-Open No. Hei 9-169622), calpronium chloride (Japanese Patent Laid-Open No. Hei 9-175950), and the like.

The present inventors have found that the hair restoring actions are synergistically enhanced by using the conventional effective ingredient for the hair-care product together with the compound selected from the fucoidan, a degradation product thereof, the sulfated monosaccharide and a salt thereof.

In other words, the present invention provides a hair-care product comprising a compound selected from the fucoidan, a degradation product thereof, the sulfated monosaccharide and a salt thereof, and the hair restoring action-enhancing component, for instance, conventional effective ingredient for the hair-care product.

The above-mentioned hair restoring action-enhancing component may be those showing synergistically enhanced hair restoring action, when used together with the compound selected from the fucoidan, a degradation product thereof, the sulfated monosaccharide and a salt thereof, and can be properly selected according to the method disclosed in the present invention (for instance, method described in Example 19). As the hair restoring action-enhancing component, the conventional effective ingredient for the hair-care product suitably used in the present invention is exemplified by minoxidil and calpronium chloride. Here, these can be used alone or in admixture.

In the hair-care product comprising the compound selected from the fucoidan, a degradation product thereof, the sulfated monosaccharide and a salt thereof, and the hair restoring action-enhancing component, the contents of each of the compound selected from the fucoidan, a degradation product thereof, the sulfated monosaccharide and a salt thereof, and the hair restoring action-enhancing component are not particularly limited so long as the amount can exhibit the synergistic effects thereby. The compound selected from the fucoidan, a degradation product thereof, the sulfated monosaccharide and a salt thereof is contained in an amount of preferably from 0.01 to 30% by weight, more preferably from 0.1 to 10% by weight, of the hair-care product. In addition, as the content of the hair restoring action-enhancing component, in a case of minoxidil, it is preferably from 0.1 to 5% by weight, more preferably from 0.5 to 2% by weight of the hair-care product; on the other hand, in a case of calpronium chloride, it is preferably from 0.1 to 10% by weight, more preferably from 0.5 to 5% by weight of the hair-care product. The hair-care product in which the above-mentioned effective ingredient and the hair restoring action-enhancing component used in the present invention are each contained within the range mentioned above is preferable because of its very excellent hair restoring action.

In addition, the hair-care product of the present invention may further contain a compound capable of enhancing the effects of minoxidil and/or calpronium chloride. The compound capable of enhancing the effects of minoxidil and/or calpronium chloride includes, for instance, topical retention agent such as epinephrine, tetrahydrozoline and naphazoline hydrochloride; polar solvents such as propylene glycol and 1,3-butylene glycol; crude drug extracts of Lithospermi Radix, Araliae Cordatae Rhizoma, Ephedrae Herba, Polygoni Multiflori Radix, Paracls Japonici Rhizoma or the like; panthenol ethyl ether; water-soluble chitin derivatives; and the like.

Further, as one embodiment of the present invention, there are provided cosmetics which can be used as food or beverage. The cosmetics can be prepared by containing, adding and/or diluting the fucoidan, a degradation product thereof, the sulfated monosaccharide, or a salt thereof, having skin cosmeticizing action and/or hair restoring action, and are extremely useful as, for instance, foods or beverages for cosmeticizing skin, for preventing hair loss, or restoring hair owing to its skin cosmeticizing action and/or hair restoring action.

The method for preparing the food or beverage for cosmeticizing skin, for restoring hair or the like of the present invention is not particularly limited. For instance, the manufacturing process including cooking and processing can be carried out in accordance with those generally employed for foods or beverages, as long as the compound selected from the fucoidan, a degradation product thereof, the sulfated monosaccharide and a salt thereof used in the present invention, having skin cosmeticizing action and/or hair restoring action may be contained, added and/or diluted as an effective ingredient in the resulting foods or beverages.

In this embodiment, the term "containing" refers to an embodiment of containing the effective ingredient used in the present invention in the food or beverage; the term "adding" refers to an embodiment of adding the effective ingredient used in the present invention to a raw material for the food or beverage; and the term "diluting" refers to an embodiment of adding a raw material for the food or beverage to the effective ingredient used in the present invention.

The form of food or beverage for cosmeticizing skin, for restoring hair or the like of the present invention is not particularly limited. The food or beverage includes, for instance, processed agricultural and forest products, processed stock raising products, processed marine products and the like, including processed grain products such as processed wheat products, processed starch products, processed premix products, noodles, macaronis, bread, bean jam, buckwheat noodles, wheat-gluten bread, rice noodle, fen-tiao, and packed rice cake; processed fat and oil products such as plastic fat and oil, tempura oil, salad oil, mayonnaise, and dressing; processed soybean products such as tofu products, soybean paste, and fermented soybeans; processed meat products such as ham, bacon, pressed ham, and sausage; marine products such as frozen ground fish, boiled fish paste, tubular roll of boiled fish paste, cake of ground fish, deep-fried patty of fish paste, fish ball, sinew, fish meat ham and sausage, dried bonito, products of processed fish egg, marine cans, and preserved food boiled down in soy sauce (tsukudani); milk products such as raw material milk, cream, yogurt, butter, cheese, condensed milk, powder milk, and ice cream; processed vegetable and fruit products such as paste, jam, pickled vegetables, fruit beverages, vegetable beverages, and mixed beverages; confectioneries such as chocolates, biscuits, sweet bun, cake, rice cake snacks, and rice snacks; alcohol beverages such as sake, Chinese liquor, wine, whisky, Japanese distilled liquor (shochu), vodka, brandy, gin, ram, beer, refreshing alcoholic beverages, fruit liquor, and liqueur; luxury drinks such as green tea, tea, oolong tea, coffee, soft drinks and lactic acid drinks; seasonings such as soy sauce, sauce, vinegar, and sweet rice wine; canned, binned or pouched foods such as rice topped cooked beef and vegetable, rice boiled together with meat and vegetables in a small pot, steamed rice with red beans, curry roux and rice, and other precooked foods; semi-dry or concentrated foods such as liver pastes and other spreads, soups for buckwheat noodles or wheat noodles, and concentrated soups; dry foods such as instant noodles, instant curry roux, instant coffee, powder juice, powder soup, instant soybean paste (miso) soup, precooked foods, precooked beverages, and precooked soup; frozen foods such as sukiyaki, pot-steamed hotchpotch, split and grilled eel, hamburger steak, shao-mai, dumpling stuffed with minced pork, various sticks, and fruit cocktails; solid foods; liquid foods (soups or the like); spices; and the like.

The food or beverage of the present invention is prepared by containing, adding and/or diluting a compound selected from the fucoidan, a degradation product thereof, the sulfated monosaccharide, and a salt thereof, wherein the compound has skin cosmeticizing action and/or hair restoring action, and its shape is not particularly limited as long as an amount necessary for the compound to exhibit the physiological functions is contained, including products shaped into tablets, granules, capsules or the like, which can be orally taken. Here, the fucoidan derived from an algae and a degradation product thereof having skin cosmeticizing action and/or hair restoring action are extremely useful as a health food material and as a production material for food or beverage, having both physiological action and dietary fiber function.

The content of the compound selected from the fucoidan, a degradation product thereof, the sulfated monosaccharide, and a salt thereof in the food for cosmeticizing skin, for restoring hair, or the like, of the present invention is not particularly limited, as long as the amount for exhibiting skin cosmeticizing action and/or hair restoring action is contained. The content of the compound is preferably from 0.001 to 100% by weight, more preferably from 0.01 to 10% by weight, still more preferably from 0.05 to 5% by weight. As the food for cosmeticizing skin, for restoring hair or the like, the compound selected from the fucoidan, a degradation product thereof, the sulfated monosaccharide, or a salt thereof may be directly taken as a powder or as a tablet.

In addition, the content of the compound selected from the fucoidan, a degradation product thereof, the sulfated monosaccharide, and a salt thereof in the beverage for cosmeticizing skin, for restoring hair, or the like is not particularly limited, as long as the amount for exhibiting skin cosmeticizing action and/or hair restoring action is contained. The content of the compound is preferably from 0.0001 to 10% by weight, more preferably from 0.005 to 5% by weight, still more preferably from 0.02 to 2% by weight.

The use embodiment for the food or beverage for cosmeticizing skin, for restoring hair or the like is not particularly limited. It is desired that the food or beverage is taken such that the above-mentioned effective ingredient used in the present invention is taken per day in an amount of preferably from 0.1 mg to 10 g, more preferably from 2 mg to 5 g, still more preferably from 10 mg to 2 g, from the viewpoint of effectively obtaining skin cosmeticizing effect and/or hair restoring effect.

In addition, no case of death is found even when the fucoidan, a degradation product thereof, the sulfated monosaccharide and a salt thereof used in the present invention is orally administered to a rat in a single dose of 1 g/kg.

In addition, backside of the Hartley guinea-pig is shaved, and a 3% solution of the fucoidan, a degradation product thereof, the sulfated monosaccharide and a salt thereof was administered by application to the backside for five consecutive days each in an amount of 0.05 mL, once a day. Skin irritancy is evaluated in accordance with a patch test standard (Japanese Dermatological Association) on the sixth day after the beginning of the administration, and found to be unreactive. Therefore, the skin irritancy could not be found for the fucoidan, a degradation product thereof, the sulfated monosaccharide and a salt thereof.

The cosmetics provided by the present invention are extremely useful as cosmetics for cosmeticizing skin and/or for restoring hair.

EXAMPLES

The present invention will be more concretely described below by means of Examples, without limiting the present invention thereto. Here, "%" in Examples means "% by weight" unless otherwise specified.

Example 1

(1) *Kjellmaniella crassifolia* was sufficiently dried, and thereafter 20 kg of the dried product was powdered with a free mill (manufactured by Nara Kikai Seisakusho), to give a powdered product of *Kjellmaniella crassifolia*.

In 900 liters of tap water was dissolved 7.3 kg of calcium chloride dihydrate (manufactured by Nippon Soda Co., Ltd.), and 20 kg of the powdered product of *Kjellmaniella crassifolia* was then mixed therewith. The resulting mixture was heated for 40 minutes until the liquid temperature was raised from 12° C. to 90° C. by blowing steam. Thereafter, the mixture was kept at 90° to 95° C. for 1 hour under stirring, and then cooled, to give 1100 liters of a cooled product.

Subsequently, the cooled product was subjected to solid-liquid separation with a solid-liquid separator (manufactured by West Farrier Separator, Model: CNA), to give about 900 liters of supernatant after solid-liquid separation.

The amount 360 liters of the supernatant after solid-liquid separation was concentrated up to a volume of 20 liters with FE10-FC-FUS0382 (fraction molecular weight: 30000) manufactured by DAICEL CHEMICAL INDUSTRIES, LTD. Thereafter, the steps of adding 20 liters of tap water and again concentrating the resulting liquid mixture up to a volume of 20 liters were repeated 5 times, and the concentrate was subjected to a desalting treatment, to give 25 liters of an extract derived from *Kjellmaniella crassifolia*.

One liter of the extract was lyophilized, to give 13 g of a non-stringy, dried product of fucoidan derived from *Kjellmaniella crassifolia*.

A non-stringy, dried product of fucoidan derived from *Laminaria japonica* was prepared from a lyophilized, powdered product of *Laminaria japonica* according to the method described above. Similarly, a non-stringy, dried product of fucoidan derived from *Lessonia nigrescence* was prepared from a dry powder of *Lessonia nigrescence* (trade name: Seaweed Powder, sold by Andesu Boeki K.K.).

(2) Seven grams of the dried product of fucoidan derived from *Kjellmaniella crassifolia* described in item (1) of Example 1 was dissolved in 700 mL of a 20 mM imidazole buffer (pH 8.0) containing 50 mM sodium chloride and 10% ethanol, and insoluble matters were removed by centrifugation. The supernatant after centrifugation was applied onto a DEAE-Cellulofine A-800 column (φ11.4 cm×48 cm) equilibrated with the same buffer, and then washed with the same buffer. The elution was carried out with a concentration gradient of from 50 mM to 1.95 M sodium chloride (250 mL per fraction). A total sugar content and an uronic acid content were determined by the phenol-sulfuric acid method and the carbazole-sulfuric acid method, to give Fractions 43 to 49, Fractions 50 to 55, and Fractions 56 to 67, in the order of elution. Next, these fractions were desalted by electrodialysis, and thereafter lyophilized, to give each of Fraction 1 (340 mg) from Fractions 43 to 49, Fraction II (870 mg) from Fractions 50 to 55, and Fraction III (2.64 g) from Fractions 56 to 67.

FIG. 1 shows an elution pattern of the fucoidan derived from *Kjellmaniella crassifolia* on the DEAE-Cellulofine A-800 column. In FIG. 1, the axis of ordinates is the absorbance at 530 nm as determined by the carbazole-sulfuric acid method (solid circles in the FIGURE), the absorbance at 480 nm as determined by the phenol-sulfuric acid method (open circles in the FIGURE), and the electric conductivity (mS/cm: open squares in the FIGURE), and the axis of abscissas is the fraction number.

Example 2

(1) A 2-liter Erlenmeyer flask was charged with 600 mL of a culture medium comprising an artificial sea water (manufactured by Jamarin Laboratory), pH 8.2, containing 0.25% glucose, 1.0% peptone, and 0.05% yeast extract, and then sterilized (at 120° C. for 20 minutes). *Alteromonas* sp. SN-1009 (FERM BP-5747) was inoculated into the culture medium, and cultured at 25° C. for 26 hours, to give a seed culture medium. A 30-liter jar fermentor was charged with 20 liters of a culture medium comprising an artificial sea water, pH 8.0, containing 1.0% peptone, 0.02% yeast extract, 0.2% sulfated polysaccharide described in item (2) of Example 2 described below, and 0.01% defoaming agent (manufactured by Shin-Etsu Chemical Co., Ltd., KM70), and sterilized at 120° C. for 20 minutes. After cooling, 600 mL of the above-mentioned seed culture medium was inoculated, and cultured at 24° C. for 24 hours under the conditions of 10 liters of aeration per minute and a stirring rate of 250 rotations per minute. After termination of the culture, the culture medium was centrifuged, to give cells and culture supernatant. The culture supernatant obtained was concentrated with an ultrafilter equipped with holofiber having an excluding molecular weight of 10000, and the concentrate was then subjected to salting out with an 85% saturated ammonium sulfate. Precipitates formed were harvested by centrifugation, and sufficiently dialyzed against a 20 mM Tris-HCl buffer (pH 8.2) containing an artificial sea water at a one-tenth concentration, to give 600 mL of a solution of an F-fucoidan degradation enzyme selectively acting on F-fucoidan.

(2) Two kilograms of dried *Kjellmaniella crassifolia* was powdered with a cutter mill (manufactured by Masuko Sangyo) fitted with a screen having a diameter of 1 mm, and the resulting seaweed chips were suspended in 20 liters of 80% ethanol. The suspension was stirred at 25° C. for 3 hours and filtered with a filter paper, and thereafter the residue was sufficiently washed. The residue obtained was suspended in 40 liters of a 20 mM sodium phosphate buffer, pH 6.5, which was heated to 95° C., the buffer containing 50 mM sodium chloride. The suspension was treated at 95° C. for 2 hours with occasional stirring, to extract a sulfated polysaccharide.

The suspension of the extract was filtered, to give a filtrate. Thereafter, the filtration residue was washed with 3.5 liters of 100 mM sodium chloride, to give an additional filtrate.

Both filtrates were combined, and then the temperature was lowered to 30° C. After 3000 U of alginic acid lyase (manufactured by Nagase Seikagaku Kogyo) was added to the resulting mixture, 4 liters of ethanol was added thereto. The resulting mixture was stirred at 25° C. for 24 hours. Next, the mixture was centrifuged, and the resulting supernatant was concentrated up to a volume of 4 liters with an ultrafilter equipped with holofiber having an excluding molecular weight of 100000. Further, the ultrafiltration was continued with 100 mM sodium chloride containing 10% ethanol until a colored substance was no longer filtered.

Precipitates formed in a non-filtrate solution were removed by centrifugation, and the temperature of the resulting supernatant was lowered to 5° C. The pH was adjusted to 2.0 with 0.5 N hydrochloric acid, and thereafter the formed precipitates such as a protein were removed by centrifugation. The pH of the resulting supernatant was rapidly adjusted to 8.0 with 1 N sodium hydroxide.

Next, an ultrafiltration was carried out with an ultrafilter equipped with holofiber having an excluding molecular weight of 100000, and the solvent was completely substituted with 20 mM sodium chloride, pH 8.0. Thereafter, the pH was again adjusted to 8.0, and the resulting mixture was centrifuged and then lyophilized, to give about 95 g of a sulfated polysaccharide.

(3) Two kilograms of dried *Kjellmaniella crassifolia* was powdered with a cutter mill fitted with a screen having a diameter of 1 mm, and the resulting seaweed chips were suspended in 20 liters of 80% ethanol. The resulting suspension was stirred at 25° C. for 3 hours, and filtered with a filter paper, and thereafter the residue was sufficiently washed. The residue obtained was suspended in 20 liters of a buffer (pH 8.2) containing 30 mL of a solution of the F-fucoidan degradation enzyme prepared in item (1) of the above-mentioned Example 2, 10% ethanol, 100 mM sodium chloride, 50 mM calcium chloride and 50 mM imidazole, and the resulting mixture was stirred at 25° C. for 48 hours. This suspension was filtered with a stainless screen having a screen-opening diameter of 32 µm, and the residue was washed with 10% ethanol containing 50 mM calcium chloride. Further, the residue was suspended in 10 liters of 10% ethanol containing 50 mM calcium chloride, and the suspension was stirred for 3 hours, and thereafter filtered with the stainless screen, and the residue was washed. Further, the residue was suspended under the same conditions, and the suspension was then stirred for 16 hours. The suspension was filtered with the stainless screen having a diameter of 32 µm, and the residue was washed.

The filtrate and the washings thus obtained were collected, and the combined mixture was subjected to ultrafiltration with an ultrafilter equipped with holofiber having an excluding molecular weight of 3000, thereby separating a filtered solution from a non-filtered solution.

This filtered solution was concentrated to a volume of about 3 liters with a rotary evaporator, and thereafter the concentrate was centrifuged, to give supernatant. The supernatant obtained was desalted with an electrodialyzer equipped with a membrane having an excluding molecular weight of 300. To the resulting solution was added calcium acetate so as to give a concentration of 0.1 M, and precipitates formed were removed by centrifugation. The resulting supernatant was applied onto a DEAE-Cellulofine column (amount of resin: 4 liters) previously equilibrated with 50 mM calcium acetate, and sufficiently washed with 50 mM calcium acetate and 50 mM sodium chloride. Thereafter, the elution was carried out with a concentration gradient of from 50 mM to 800 mM sodium chloride. The eluate at this time was collected 500 mL each. The collected fraction was analyzed by cellulose acetate membrane electrophoresis [*Analytical Biochemistry*, 37, 197-202 (1970)]. As a result, a sulfated saccharide which was eluted on a concentration of about 0.4 M sodium chloride (proximity of Fraction No. 63) was homogeneous.

Then, a solution of Fraction No. 63 was first concentrated to a volume of 150 mL, and thereafter sodium chloride was added so as to give a concentration of 4 M. The resulting solution was applied onto a Phenyl-Cellulofine column (amount of resin: 200 mL) previously equilibrated with 4 M sodium chloride, and sufficiently washed with 4 M sodium chloride. Non-adsorptive sulfated saccharide fractions were collected, and desalted with an electrodialyzer equipped with a membrane having an excluding molecular weight of 300, to give 505 mL of a desalted solution.

Forty milliliters of the desalted solution obtained was applied onto a Cellulofine GCL-90 column (4.1 cm×87 cm) equilibrated with 0.2 M sodium chloride containing 10% ethanol, to perform gel filtration. The collection was performed at 9.2 mL per fraction.

All of the fractions were analyzed for a total sugar content by the phenol-sulfuric acid method [*Analytical Chemistry*, 28, 350 (1956)].

As a result, since the sulfated saccharide formed a single peak, Fraction Nos. 63 to 70, which were fractions corresponding to a central part of the peak were collected. The combined fraction was desalted with an electrodialyzer equipped with a membrane having an excluding molecular weight of 300, and thereafter lyophilized, to give 112 mg of a dried product of the compound represented by the following formula (VIII). The compound is hereinafter referred to as 7-12SFd-F.

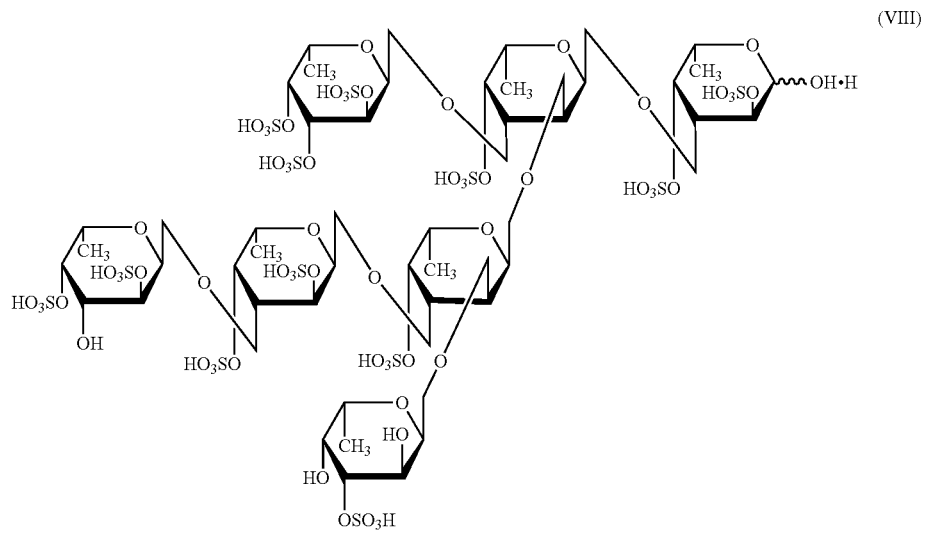

(VIII)

(4) To 80 mL of a 2.5% aqueous solution of Fraction III (F-fucoidan) prepared in item (2) of Example 1 were added 16 mL of 1 M Tris-HCl buffer (pH 7.6), 16 mL of a 1 M aqueous CaCl$_2$ solution, 24 mL of a 4 M aqueous NaCl solution, 8 mL of the solution of the F-fucoidan degradation enzyme obtained in item (1) of Example 2 and 176 mL of distilled water, and the resulting mixture was heated at 30° C. for 3 hours. The resulting enzymatically treated F-fucoidan solution was concentrated with a rotary evaporator so as to give a final concentration of the enzymatically treated F-fucoidan of 2%, and thereafter the concentrate was dialyzed in distilled water, to give a 2% aqueous solution of the enzymatically treated F-fucoidan. This sample was analyzed by HPLC (column: SB802.5; column temperature: 35° C.; mobile phase: 50 mM NaCl; flow rate: 0.5 mL/min; detection: RI ATT=8). As a result, it was revealed that about 40% of the sample was 7-12SFd-F as shown by the formula (VIII).

Example 3

(1) Two kilograms of dried *Kjellmaniella crassifolia* was powdered with a cutter mill (manufactured by Masuko Sangyo) fitted with a screen having a hole diameter of 1 mm. After the powdered product was stirred in 20 liters of 80% ethanol at 25° C. for 3 hours, the mixture was filtered, and the residue was washed. The resulting residue was suspended in 20 liters of a 30 mM imidazole buffer (pH 8.2) containing 50 mM calcium chloride, 100 mM sodium chloride, 10% ethanol, and 1 U of *Alteromonas* sp. SN-1009 (FERM BP-5747) F-fucoidan degradation enzyme prepared in item (1) of Example 2. The resulting suspension was stirred at 25° C. for 2 days, and thereafter filtered with a stainless screen having a hole diameter of 32 μm, and the residue was washed. The resulting residue was suspended in 40 liters of a sodium phosphate buffer (pH 6.6) containing 100 mM sodium chloride, 10% ethanol and 4 g of an alginic acid lyase (manufactured by Nagase Seikagaku Kogyo). The resulting suspension was stirred at 25° C. for 4 days, and thereafter centrifuged, to give supernatant. In order to remove low-molecular weight products of alginic acid contained in the supernatant obtained, the supernatant was concentrated to a volume of 2 liters with an ultrafilter equipped with holofiber having an excluding molecular weight of 100000, and thereafter the solvent was exchanged for 100 mM sodium chloride containing 10% ethanol. To the resulting solution was added with stirring an equivolume of 400 mM calcium acetate, and thereafter the mixture was centrifuged. The pH of the resulting supernatant was adjusted to 2 with 1 N hydrochloric acid, with cooling on ice. Precipitates formed were removed by centrifugation, and the pH of the resulting supernatant was adjusted to 8.0 with 1 N sodium hydroxide. This solution was concentrated to a volume of 1 liter by ultrafiltration, and thereafter the solvent was exchanged for 100 mM sodium chloride. Precipitates formed at this time were removed by centrifugation. In order to remove hydrophobic substances in the resulting supernatant, sodium chloride was added to the supernatant so as to give a concentration of 1 M, and the resulting mixture was applied onto a column containing 3 liters of Phenyl-Cellulofine (manufactured by Seikagaku Corporation) equilibrated with 1 M sodium chloride, to collect an effluent fraction. The fraction was concentrated with an ultrafilter, and thereafter the solvent was exchanged for 20 mM sodium chloride. The resulting solution was lyophilized, and the weight of the lyophilized product was 29.3 g.

(2) Fifteen grams of the above-mentioned lyophilized product was dissolved in 1.5 liters of 50 mM Tris-HCl buffer containing 400 mM sodium chloride and 9 U of an endo-sulfated polysaccharide-degrading enzyme (U-fucoidan degradation enzyme) obtained from a culture prepared by culturing *Flavobacterium* sp. SA-0082 (FERM BP-5402) disclosed in WO97/26896. After the resulting solution was subjected to the reaction at 25° C. for 6 days, the reaction mixture was concentrated to a volume of about 300 mL with an evaporator. The concentrate was placed in a dialysis tube having an excluding molecular weight of 3500 and thoroughly dialyzed. The solution remaining in the dialysis tube was applied onto a column containing 4 liters of DEAE-Cellulofine A-800 equilibrated with 50 mM sodium chloride, and sufficiently washed with 50 mM sodium chloride. Thereafter, the elution was carried out on a concentration gradient of from 50 to 650 mM sodium chloride. Further, the elution was sufficiently carried out in the same column with 650 mM sodium chloride. Among the eluted fractions, the fractions eluted with 650 mM sodium chloride were collected as a sulfated fucogalactan fraction, and concentrated with an ultrafilter having an excluding molecular weight of 100000. Thereafter, the solvent was substituted with 10 mM sodium chloride, and the resulting solution was lyophilized, to give 0.85 g of a non-stringy, lyophilized product of sulfated fucogalactan. The sulfated fucogalactan obtained (G-fucoidan) was found to contain galactose and fucose as constituting saccharides in a molar ratio of about 2:1.

(3) For the production of G-fucoidan degradation enzyme, 600 mL of a culture medium comprising an artificial sea water (manufactured by Jamarin Laboratory), pH 7.5, containing 0.1% glucose, 1.0% peptone, and 0.05% yeast extract was sterilized at 120° C. for 20 minutes, and thereafter *Flavobacterium* sp. SA-0082 (FERM BP-5402) was inoculated into the culture medium and cultured at 24° C. for 23 hours, to give a seed culture medium. A 30-liter jar fermentor was charged with 20 liters of a culture medium comprising an artificial sea water (pH 7.5) containing 0.2% fucoidan fraction derived from *Kjellmaniella crassifolia* prepared by the method of item (1) of Example 3, 2.0% peptone, 0.01% yeast extract, and 0.01% defoaming agent (manufactured by Shin-Etsu Chemical Co., Ltd., KM70), and sterilized at 120° C. for 20 minutes. After cooling, 600 mL of the above-mentioned seed culture medium was inoculated, and cultured at 24° C. for 23 hours under the conditions of 10 liters of aeration per minute and a stirring rate of 125 rotations per minute. After termination of the culture, the culture medium was centrifuged, to give cells.

The cells obtained were suspended in 1200 mL of a 10 mM Tris-HCl buffer (pH 8.0) containing 0.4 M sodium chloride, and subjected to ultrasonic disruption. Thereafter, the resulting product was centrifuged, to give a cell extract. The cell extract obtained was sufficiently dialyzed against the same buffer, and centrifuged, to give supernatant. To the resulting supernatant was added ammonium sulfate so as to give a final concentration of 90% saturation, and precipitates formed were collected by centrifugation. The precipitates obtained were dissolved in 150 mL of a 10 mM Tris-HCl buffer (pH 8.0) containing 50 mM sodium chloride. The resulting solution was sufficiently dialyzed against the same buffer, and centrifuged. The supernatant obtained was applied onto a 500-mL DEAE-Sepharose FF column (manufactured by Amersham-Pharmacia) equilibrated with the same buffer, and washed with the same buffer. Thereafter, the elution was carried out with a concentration gradient of from 50 mM to 600 mM sodium chloride, to collect an active fraction.

The active fraction obtained was sufficiently dialyzed against a 10 mM Tris-HCl buffer (pH 8.0) containing 0.1 M sodium chloride, applied onto a column containing 100 mL of DEAE-Cellulofine A-800 (manufactured by CHISSO CORPORATION) equilibrated with the same buffer, and washed with the same buffer. T hereafter, the elution was carried out with a concentration gradient of from 0.1 M to 0.4 M sodium chloride, to collect an active fraction. Sodium chloride was added to the resulting active fraction so as to give a concentration of 4 M. The solution obtained was applied onto a column containing 20 mL of Phenyl-Cellulofine (manufactured by CHISSO CORPORATION) equilibrated with a 10 mM Tris-HCl buffer (pH 8.0) containing 4 M sodium chloride, and washed with the same buffer. Thereafter, the elution was carried out with a concentration gradient of from 4 M to 1 M sodium chloride. Subsequently, a sufficient elution was further carried out with a 10 mM Tris-HCl buffer (pH 8.0) containing 1 M sodium chloride, to collect an active fraction. Sodium chloride was added to the active fraction obtained so as to give a concentration of 3 M. The resulting solution was applied onto a column containing 10 mL of Phenyl-Cellulofine (manufactured by CHISSO CORPORATION) equilibrated with a 10 mM Tris-HCl buffer (pH 8.0) containing 3 M sodium chloride, and washed with the same buffer. Thereafter, the elution was carried out with a concentration gradient of from 3 M to 0.5 M sodium chloride. Subsequently, a sufficient elution was further carried out with a 10 mM Tris-HCl buffer (pH 8.0) containing 0.5 M sodium chloride, to collect an active fraction. The purified enzyme thus obtained was used as G-fucoidan degradation enzyme.

(4) G-fucoidan described in item (2) of Example 3 was treated with the above purified G-fucoidan degradation enzyme, to prepare a low-molecular weight product. Specifically, 1.94 g of G-fucoidan was dissolved in a 25 mM Tris-HCl buffer (pH 8.0) containing 0.2 M sodium chloride. Thereafter, 186 mU of G-fucoidan degradation enzyme was added thereto, and the resulting solution was subjected to the reaction at 25° C. for 6 days. The reaction mixture was concentrated to a volume of 80 mL with an evaporator. The concentrate was applied onto a Cellulofine GCL-1000 column (4×90 cm) (manufactured by CHISSO CORPORATION) for molecular weight fractionation. The fractions having a molecular weight of 15000 or less were collected, and the combined fraction is referred to as a G-fucoidan degradation enzyme-digested fraction.

(5) The above G-fucoidan enzyme-digested fraction was concentrated to a volume of 500 mL with an evaporator, and thereafter the concentrate was desalted with an electrodialyzer. The resulting desalted product was applied onto a column containing 1 liter of DEAE-Cellulofine A-800 (manufactured by CHISSO CORPORATION) previously equilibrated with a 10 mM imidazole-hydrochloric acid buffer (pH 8) containing 10 mM sodium chloride, and washed with the same buffer. Thereafter, the elution was carried out with a concentration gradient of from 10 mM to 900 mM sodium chloride. The eluate was collected 61 mL each, and each of its sugar content was determined by the phenol-sulfuric acid method. The fractions eluted with proximity of 270 mM sodium chloride were collected since they formed a peak of sugar content, and the combined fraction is referred to as 270 mM-eluted fraction (ii).

In addition, to the above-mentioned 270 mM-eluted fraction (ii) was added water so as to have the same electric conductivity as that of a 10 mM imidazole-hydrochloric acid buffer (pH 8) containing 150 mM sodium chloride, and the resulting solution was applied onto a column containing 200 mL of DEAE-Cellulofine A-800 (manufactured by CHISSO CORPORATION) previously equilibrated with a 10 mM imidazole-hydrochloric acid buffer (pH 8) containing 150 mM sodium chloride and washed with the same buffer. Thereafter, the elution was carried out with a concentration gradient of from 150 mM to 300 mM sodium chloride. The eluate was collected 12 mL each, and each of its sugar content was determined by the phenol-sulfuric acid method. Fractions eluted with proximity of from 160 mM to 180 mM sodium chloride were collected, and concentrated to a volume of 2 mL with a speed vac (manufactured by SAVANT Instruments Inc.). Thereafter, the concentrate was applied onto a column containing 200 mL of Cellulofine GCL-25 (manufactured by CHISSO CORPORATION) previously equilibrated with 10% ethanol solution, and the elution was carried out with the same solution. The eluate was collected 2 mL each, and each of its sugar content was determined by the phenol-sulfuric acid method. Fractions forming a peak of sugar content were collected, and referred to as (D).

The above Fraction (D) was desalted with an electrodialyzer, and thereafter lyophilized. The composition of sugars and the molecular weight were analyzed. In addition, the structural analysis was carried out by NMR analysis after substitution with heavy water by a prescribed method.

Properties of (D)

Molecular weight; 1358

$^1$H-NMR (D2O)

δ; 5.19 (1H, d, J=4.3 Hz, F1-1-H), 4.93 (1H, d, J=3.7 Hz, F2-1-H), 4.62 (1H, overlapped with HOD, G1-1-H), 4.59 (1H, overlapped with HOD, G2-1-H), 4.54 (1H, d-d, J=10.6, 2.7 Hz, F1-3-H), 4.46 (1H, d, J=7.6 Hz, G3-1-H), 4.46 (1H, m, F2-3-H), 4.41 (1H, br-s, G2-4-H), 4.41 (1H, d, J=7.6 Hz, G4-1-H), 4.37 (1H, q, J=6.4 Hz, F2-5-H), 4.27 (1H, m, G2-3-H), 4.24 (1H, br-s, G3-4-H), 4.21 (1H, m, G3-3-H), 4.19 (1H, m, G4-3-H), 4.15 (1H, br-s, G4-4-H), 4.13 (1H, q, J=6.7 Hz, F1-5-H), 4.09 (1H, d, J=2.7 Hz, F1-4-H), 4.04 (1H, d, J=2.8 Hz, F2-4-H), 3.98 (1H, m, G2-6-H), 3.96 (1H, d-d, J=10.6, 4.3 Hz, F1-2-H), 3.93 (1H, m, G3-6-H), 3.88 (1H, br-s, G1-4-H), 3.86 (1H, m, G2-5-H), 3.81 (1H, m, G2-6-H), 3.81 (1H, m, F2-2-H), 3.80 (1H, m, G3-5-H), 3.80 (1H, m, G3-6-H), 3.66 (1H, m, G1-3-H), 3.65 (1H, m, G2-2-H), 3.64 (1H, m, G1-6-H), 3.64 (1H, m, G4-6-H), 3.61 (1H, m, G4-5-H), 3.58 (1H, m, G1-2-H), 3.56 (1H, m, G1-6-H), 3.56 (1H, m, G4-6-H), 3.55 (1H, m, G4-2-H), 3.54 (1H, m, G1-5-H), 3.54 (1H, m, G3-2-H), 1.20 (3H, d, J=6.7,F1-6-H), 1.14 (3H, d, J=6.4, F2-6-H)

Composition of sugars (molar ratio): L-fucose: D-galactose=2:4

Sulfate group: 5 molecules

Here, the numbers assigned to the peaks in the $^1$H-NMR are as show in the following formula (IX). The compound is hereinafter referred to as 6-5SFd-G.

10 U of the F-fucoidan degradation enzyme prepared in item (1) of Example 2. The resulting suspension was stirred at 25° C. for 3 days, and subjected to an ultrafiltration with an ultrafilter equipped with holofiber having an excluding molecular weight of 100000, with adding the above-mentioned buffer.

The amount 34 U of U-fucoidan degradation enzyme described in item (2) of Example 3 was added to the ultrafiltrated solution, and the resulting mixture was stirred at 25° C. for 2 days and subjected to an ultrafiltration with an is ultrafilter equipped with holofiber having an excluding molecular weight of 100000, with adding water.

The filtrate was collected, and concentrated to a volume of 1.5 liters with an evaporator. Thereafter, the concentrate was completely desalted with a desalting apparatus, applied onto a column containing 3 liters of DEAE-Cellulofine A-800 previously equilibrated with 5 mM imidazole-hydrochloric acid buffer (pH 6.5) containing 30 mM sodium chloride, and washed with 6 liters of the same buffer. Thereafter, the elution was carried out with a concentration gradient of from 30 mM to 500 mM sodium chloride. The amount of the solution required for the elution was 48 liters. The eluate was collected 180 mL each, and its sugar content was determined by the phenol-sulfuric acid method. In addition, the absorbance at 232 nm was determined at the same time. The fractions eluted with 130 mM to 170 mM sodium chloride were collected since they formed a single peak. The combined fraction was

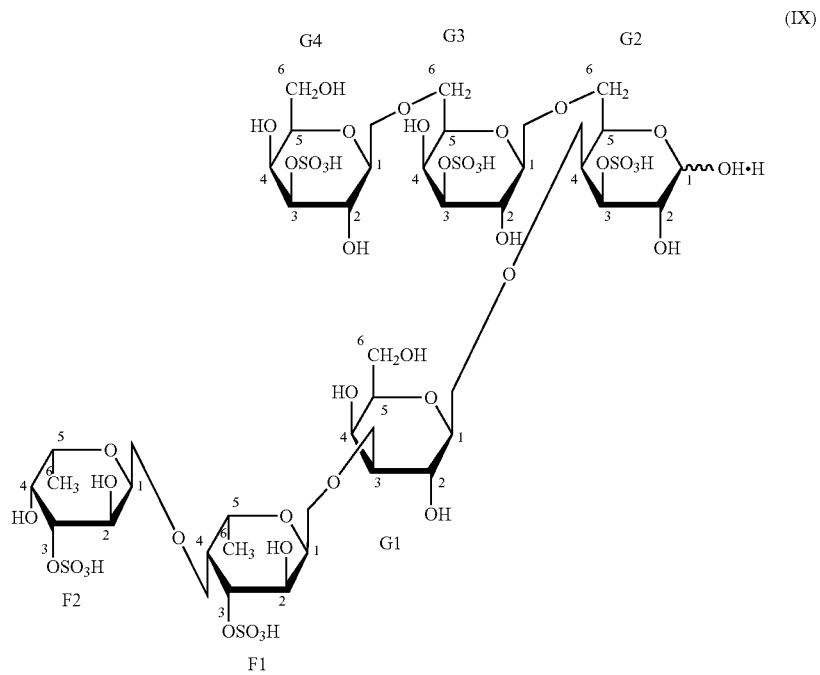

(IX)

Example 4

One-hundred and twenty grams of the sulfated polysaccharide prepared in item (2) of Example 2 was suspended in 8 liters of a 20 mM imidazole buffer (pH 7.5) containing 20 mM calcium chloride, 300 mM sodium chloride, 10% ethanol and desalted with a desalting apparatus, and thereafter lyophilized, to give 5.85 g of an oligosaccharide. It was confirmed that this oligosaccharide has a molecular weight of 1128 by mass spectrometry, and that it is the compound represented by the following formula (X) by NMR analysis. The compound is hereinafter referred to as 6-2SFd-U.

(X)

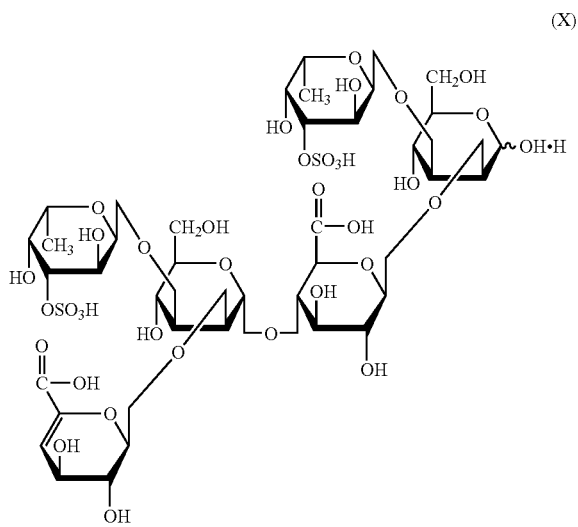

Example 5

(1) Five-hundred grams of *Kjellmaniella crassifolia* was cut into thin pieces, and washed with 10 liters of 80% ethanol. Thereafter, the resulting product was stirred in a container having an inner diameter of 40 cm containing 50 liters of 10% ethanol containing 1 mM potassium chloride at 25° C. for 2 days, at a speed of 120 rotations per minute to extract fucoidan. The resulting extract was filtered with a stainless screen having a screen diameter of 32 μm, to give a fucoidan solution.

To 46 liters of the fucoidan solution was added one liter of a palm oil solution with stirring, the palm oil solution being prepared by dissolving 1 g of palm oil (manufactured by Kao Corporation, for cosmetic use) in 1 liter of ethanol, and one liter of glycerol was further added thereto, to give a lotion. Also, lotions were prepared using the fucoidan and a degradation product thereof described in each Example in the same manner.

(2) To the fucoidan solution prepared in item (1) of Example 5, gelatin and perfume were each added so as to have a final concentration of 0.02%, to give a lotion containing gelatin. Also, collagen was similarly added, to give a lotion containing collagen. In addition, lotions were prepared using the fucoidan and a degradation product thereof described in each Example in the same manner.

(3) A perfume was added to the fucoidan prepared in item (1) of Example 5, to prepare a hair lotion. Similarly, hair lotions were prepared using the fucoidan and a degradation product thereof described in each Example.

Example 6

One kilogram of a dried product of a commercially available sporophyll of *Undaria pinnatifida* (Wakame Mekabu) was powdered with a cutter mill fitted with a screen having a hole diameter of 1 mm. Thereafter, the powdered sporophyll was suspended in 10 liters of 80% ethanol, and the suspension was stirred for 3 hours, and thereafter filtered with a filter paper, to give a residue. The residue was suspended in 20 liters of a 40 mM phosphate buffer (pH 6.5) containing 50 mM sodium chloride, and treated at 95° C. for 2 hours. The treated solution was cooled to 37° C., and thereafter ethanol was added thereto so as to give a concentration of 10%. After 12000 U of a commercially available alginic acid lyase K (manufactured by Nagase Seikagaku Kogyo) was added thereto, and the mixture was stirred at room temperature for 24 hours. The resulting treated solution was centrifuged, and the supernatant was concentrated to a volume of 2 liters with an ultrafilter equipped with holofiber having an excluding molecular weight of 100000. Thereafter, precipitates formed were removed by centrifugation. The resulting supernatant was cooled to 5° C., and thereafter 0.5 N hydrochloric acid was added thereto to adjust the pH to 2.0. Subsequently, the resulting mixture was stirred for 30 minutes, and precipitates formed were removed by centrifugation. The pH of the supernatant was adjusted to 8.0 with 0.5 N sodium hydroxide, and the solvent was substituted with 20 mM sodium chloride by ultrafiltration. The pH of the resulting solution was adjusted to 8.0, and thereafter the supernatant obtained after centrifugation was lyophilized, to give 90.5 g of non-stringy fucoidan derived from sporophyll of *Undaria pinnatifida*.

Example 7

One kilogram of a dried product of powdered *Fucus vesiculosus* was suspended in 10 liters of 80% ethanol, and the suspension was stirred for 3 hours, and thereafter filtered with a filter paper, to give a residue. The residue was suspended in 30 liters of a 30 mM phosphate buffer (pH 6.0) containing 100 mM sodium chloride, and treated at 95° C. for 2 hours. After the treated solution was cooled to 37° C., 100 g of activated carbon was added, and the mixture was stirred for 30 minutes. After 3000 U of a commercially available alginic acid lyase K was added, ethanol was added so as to give a concentration of 10%, and the resulting mixture was stirred at room temperature for 24 hours. The resulting treated solution was centrifuged, and the supernatant was concentrated to a volume of 2 liters with an ultrafilter equipped with holofiber having an excluding molecular weight of 100000. Thereafter, precipitates formed were removed by centrifugation, and the supernatant was ultrafiltered with an extract added, to remove a pigment. The non-filtered solution obtained was cooled to 5° C., and thereafter 0.5 N hydrochloric acid was added thereto to adjust the pH to 2.0. Subsequently, the resulting solution was stirred for 30 minutes, and precipitates formed were removed by centrifugation. The pH of the supernatant was adjusted to 8.0 with 0.5 N sodium hydroxide, and the solvent was substituted with 20 mM sodium chloride by ultrafiltration. The pH of the resulting solution was adjusted to 8.0, and thereafter the supernatant obtained after centrifugation was lyophilized, to give 71 g of non-stringy fucoidan derived from *Fucus vesiculosus*.

Non-stringy fucoidan derived from *Ascophyllum nodosum* was prepared from a dry powder of *Ascophyllum nodosum* (trade name: Algin Gold, sold by Andesu Boeki K.K.) according to the method described above.

Example 8

Two grams of the fucoidan derived from *Kjellmaniella crassifolia* prepared by the method described in item (1) of Example 1 was dissolved in 100 mL of water, and the pH of the solution was adjusted to 3 with citric acid. Thereafter, the resulting mixture was treated at 100° C. for 3 hours, to give a product decomposed with the acid of the fucoidan. This hydrolysate was subjected to molecular weight fractionation by gel filtration on Cellulofine GCL-300 or Cellulofine GCL-25, into fractions of a molecular weight exceeding 25000 (Fraction A), exceeding 10000 to 25000 (Fraction B) and exceeding 5000 to 10000 (Fraction C) using Cellulofine GCL-300; and exceeding 2000 to 5000 (Fraction D), exceeding 500 to 2000 (Fraction E) and 500 or less (Fraction F) using Cellulofine GCL-25. Further, each of these fractions and the product decomposed with the acid were desalted, and then lyophilized, to give the product decomposed with the acid and each fraction of the product decomposed with the acid.

Example 9

Five kilograms of a commercially available, salt-preserved *Nemacystus decipiens* was cut into thin pieces with scissors, and mixed with 20 liters of ethanol. The resulting mixture was allowed to stand overnight, and then filtered with a filter paper. The resulting residue was suspended in 12.5 liters of water, and treated at 95° C. for 2 hours. After the treated solution was filtered with a filter paper, 2600 mL of a 2.5% cetyl pyridinium chloride solution containing 350 mM sodium chloride was added thereto, and the resulting mixture was allowed to stand for 3 days. The supernatant portion was discarded, the precipitate portion was centrifuged, and the resulting supernatant was also discarded. To the precipitates obtained was added 2.5 liters of 350 mM sodium chloride, and thereafter the mixture was homogenized with a homogenizer and centrifuged. The washing steps were repeated 3 times. Four-hundred milliliters of 400 mM sodium chloride was added to the precipitates obtained. Thereafter, the mixture was homogenized with a homogenizer, and ethanol was added thereto so as to give a concentration of 80%. The mixture was stirred for 30 minutes, and then filtered with a filter paper. Five hundred milliliters of 80% ethanol saturated with sodium chloride was added to the residue obtained, and thereafter the mixture was homogenized with a homogenizer. Ethanol saturated with sodium chloride was added to make up a volume of 1 liter, and the mixture was stirred for 30 minutes and then filtered with a filter paper. The washing steps were repeated until the absorbance at 260 nm of the filtrate became 0 (zero) (usually 5 times). The residue obtained was dissolved in 1.5 liters of 2 M sodium chloride, and thereafter insoluble matters were removed by centrifugation. The resulting solution was allowed to flow through a column containing 100 mL of DEAE-Cellulofine A-800 previously equilibrated with 2 M sodium chloride. Effluent fractions were concentrated to a volume of 2 liters with an ultrafilter equipped with holofiber having an excluding molecular weight of 100000, and thereafter the solvent was substituted with 2 mM sodium chloride by an ultrafilter. The resulting solution was centrifuged, and the resulting supernatant was lyophilized, to give 22.9 g of fucoidan derived from *Nemacystus decipiens*.

Example 10

(1) Fifty grams of a dried *Gelidium amansii* was cut into thin pieces with scissors, and suspended in 500 mL of 80% ethanol. Thereafter, the resulting suspension was stirred at 25° C. for 3 hours, and filtered with a filter paper. The resulting residue was suspended in 1 liter of a 30 mM sodium phosphate buffer (pH 6.5) containing 100 mM sodium chloride, treated at 95° C. for 2 hours, and thereafter filtered with a stainless screen having a hole diameter of 106 μm. The above-mentioned sodium phosphate buffer was added to the filtrate obtained to make up a volume of 3 liters. Five grams of activated carbon was added thereto, and the resulting mixture was stirred at 25° C. overnight, and then centrifuged. The resulting supernatant was concentrated to a volume of 200 mL with an ultrafilter equipped with holofiber having an excluding molecular weight of 100000, and thereafter subjected to solvent-exchange with an ultrafilter to give a 10 mM sodium chloride solution. Insoluble matters in the solution were removed by centrifugation, and thereafter the resulting solution was lyophilized, to give 2.3 g of a dried product of a sulfated polysaccharide fraction derived from *Gelidium amansii*.

(2) According to the method described in item (1) of Example 10, 4.4 g of a sulfated polysaccharide derived from *Gracilaria verrucosa* was prepared from 50 g of dried *Gracilaria verrucosa*. Similarly, 1.0 g of a sulfated polysaccharide derived from *Pterocladiella capillacea* was also prepared from a dried *Pterocladiella capillacea*.

(3)-[1] One kilogram of a commercially available powder of dried *Lessonia nigrescence* was suspended in 10 liters of 80% ethanol, and thereafter the resulting suspension was stirred at 25° C. for 3 hours and filtered with a filter paper. The resulting residue was suspended in 20 liters of a 30 mM sodium phosphate buffer (pH 6.5) containing 100 mM sodium chloride, and the resulting suspension was treated at 95° C. for 2 hours, and thereafter filtered with a stainless screen having a hole diameter of 106 μm. To the resulting filtrate were added 100 g of activated carbon, 2.4 liters of ethanol and 6000 U of alginic acid lyase K, and the resulting mixture was stirred at 25° C. for 22 hours and then centrifuged. The resulting supernatant was concentrated to a volume of 1.2 liters with an ultrafilter equipped with holofiber having an excluding molecular weight of 100000, and thereafter insoluble matters were removed by centrifugation. The resulting solution was allowed to stand at 5° C. for 24 hours. Formed precipitates were removed by centrifugation, and the resulting supernatant was subjected to solvent-exchange with an ultrafilter to give a 100 mM sodium chloride solution. After the solution was cooled to 4° C. or lower, the pH was adjusted to 2.0 with hydrochloric acid, and the formed precipitates were removed by centrifugation. The pH of the resulting supernatant was adjusted to 8.0 with sodium hydroxide, and the resulting solution was concentrated to a volume of 2 liters. Thereafter, the solvent was exchanged for 20 mM sodium chloride by using an ultrafilter. Insoluble matters in the resulting solution were removed by centrifugation, and thereafter the resulting product was lyophilized, to give 41 g of a non-stringy, dried product of a fraction of fucoidan derived from *Lessonia*.

(3)-[2] Six grams of the above-mentioned lyophilized product was dissolved in 600 mL of a 20 mM imidazole-hydrochloric acid buffer (pH 6) containing 100 mM sodium chloride, and the resulting solution was applied onto a column containing 5 liters of DEAE-Cellulofine A-800 previously equilibrated with the same buffer. After washing was carried out with 10 liters of the same buffer, the elution was carried out with a concentration gradient of from 100 to 1600 mM sodium chloride. The amount of the solution used for the elution was 13 liters, and the eluate was collected 500 mL each. Of the eluted fractions, 500 mL each of the eluted fractions obtained at proximity of 250 mM, 530 mM and 700 mM sodium chloride concentration was dialyzed against purified water, and lyophilized. The lyophilized products were named DEAE Fraction 33, DEAE Fraction 37 and DEAE Fraction 40, respectively, and obtained in the amounts of 57 mg, 24 mg and 62 mg, respectively.

Example 11

Five kilograms of sea cucumbers were dissected, and the organs were removed to collect somatic layers. Five-hundred milliliters of acetone was added per 200 g of the wet weight of the somatic layers, and the mixture was treated with a homogenizer. Thereafter, the homogenate was filtered, and the residue was washed with acetone until no more colored substances remained. This residue was dried with suction, to give 140 g of a dried product. To this dried product was added 2.8 liters of a 0.4 M saline, and the mixture was treated at 100° C. for 1 hour. Thereafter, the mixture was filtered, and the residue was sufficiently washed with a 0.4 M saline, to give 3.7 liters of an extract. To this extract was added 5% cetyl pyridinium chloride until no more precipitates were formed, and the formed precipitates were harvested by centrifugation. The precipitates were suspended in a 0.4 M saline, and again centrifuged. One liter of a 4 M saline was added to the resulting precipitates, and the mixture was treated with a homogenizer. Thereafter, 4 liters of ethanol was added thereto with stirring, and the resulting mixture was stirred for 1 hour, and thereafter filtered, to give precipitates. The steps of suspending the precipitates in 80% ethanol and thereafter filtering the suspension were repeated until the absorbance at 260 nm of the supernatant became almost zero (0). The precipitates obtained were suspended in 2 liters of a 2 M saline, and insoluble matters were removed by centrifugation. The supernatant was ultrafiltered with an ultrafilter equipped with a membrane having an excluding molecular weight of 30000, and completely desalted. Thereafter, the resulting product was lyophilized, to give 3.7 g of fucoidan derived from sea cucumbers.

Example 12

(1) Six-hundred and twenty-five grams of a commercially available, salt-preserved *Cladosiphon okamuranus* was suspended in 4375 mL of a 30 mM sodium phosphate buffer (pH 6.0), and the suspension was treated with a homogenizer at 8000 rotations per minute for 5 minutes. Thereafter, the homogenate was treated at 95° C. for 1 hour, and centrifuged, to give supernatant. Ten grams of activated carbon was added to the supernatant obtained. Thereafter, the resulting mixture was stirred for 30 minutes, and centrifuged, to give supernatant. The resulting supernatant was concentrated to a volume of 2 liters with an ultrafilter equipped with holofiber having an excluding molecular weight of 100000. Thereafter, the solvent was substituted with a 20 mM sodium chloride, and the resulting solution was lyophilized, to give 10.9 g of a non-stringy, dried product of a fucoidan derived from *Cladosiphon okamuranus*.

(2) The fucoidan was treated with the fucoidan degradation enzyme produced by *Fucophilus fucoidanolyticus* SI-1234 (FERM P-17517). The resulting enzymatically degraded products were analyzed by instrumental analysis such as NMR and MASS. As a result, the fucoidan was found to be a fucoidan having the structure represented by the above-mentioned general formula (IV) as a repeating unit. In addition, the fucoidan was a fucoidan containing fucose and glucuronic acid in a molar ratio of from 35:10 to 44:10, and having an average molecular weight of about 1000000.

Example 13

(1) Male C3H/He mice were purchased from Nippon SLC and used for an experiment from 5 week-old after pre-breeding the mice. The fucoidan derived from *Kjellmaniella crassifolia* prepared in item (1) of Example 1 was suspended and dissolved in ethanol in a concentration of 3%, and the resulting solution was applied onto the backside of the mice in an amount of 200 µL per mouse. To the control group, ethanol was similarly applied. The mice were administered once a day, for 8 consecutive days. Hair on the backside was partially removed on ninth day after the beginning of administration, and the length of hair was measured under the microscope using a caliper. In addition, skin was peeled off after the mice were sacrificed by exsanguination, and the color of the backside skin was analyzed using an image analysis software (NIH Image).

The results are shown in Table 1. In the table, the length of hair is expressed by an average value±standard error of 5 cases, and the skin color is expressed by an average color tone of darkness of 5 cases when the color tone of the control group is defined as 100.

In the control group, a state of transition to the telogen was apparently observed, and the skin color had been white. On the other hand, the fucoidan-administered group maintained the anagen, and the skin color was more grayish than that of the control group. The length of hair was longer in the fucoidan-administered group than that of the control group. In other words, a hair restoring effect was confirmed in the fucoidan-administered group.

TABLE 1

|  | Length of Hair (mm) | Skin Color |
| --- | --- | --- |
| *Kjellmaniella crassifolia*-derived Fucoidan-Administered Group (N = 5) | 6.86 ± 0.20 | 125 |
| Control Group (N = 5) | 6.38 ± 0.19 | 100 |

Average Value ± Standard Error

C3H/He mice are frequently used for the evaluation of hair restoring effect. The hair of a 5-week mouse is in the anagen during which the hair and the hair follicles actively grow. During this stage, pigments and enzymes are actively secreted in the hair follicle cells, so that the skin color is observed to be considerably dark. However, when the state of the hair begins to transfer to the telogen from the anagen, the hair stops growing and the hair follicles become smaller, so that the secreting function is weakened. Therefore, the skin color gradually becomes lighter, so that the color is observed to be pinkish to whitish. Although the hair cycle proceeds physiologically by nature, if the anagen can be maintained, the proportion of the growing hair will be increased. An agent having such a function can be useful for a hair-care product (*The Journal of Dermatology* 10: 45-54, 1983.).

In addition, similar tests were carried out for the fucoidan and a degradation product thereof described in each Example. As a result, similar hair restoring effects could be confirmed.

(2) Male C3H/He mice were purchased from Nippon SLC and used for an experiment from 8 week-old after pre-breeding the mice. The hair on the backside of each mouse was cut with hair clippers.

The fucoidan derived from *Kjellmaniella crassifolia* prepared in item (1) of Example 1 was suspended and dissolved in ethanol in a concentration of 3%, and the resulting solution was applied onto the above-mentioned hair-cut site of the backside of the mice in an amount of 200 µL per mouse. To the control group, ethanol was similarly applied. The mice were administered once a day, for consecutive days.

The administered site was observed over the passage of time from the beginning of administration, and a change in the skin color tone was evaluated by scoring. Specifically, the scoring criteria were defined as follows: Score 0: no change in the skin color, Score 1: the skin color being changed to blue, Score 2: the skin color being changed to black-blue to gray, Score 3: trichogenous state being observed, and Score 4: the state before the hair cutting being almost restored.

The average score for each group was calculated. The results are shown in Table 2.

As shown in Table 2, the *Kjellmaniella crassifolia*-derived fucoidan-administered group showed a change in the skin color and an acceleration of hair growth from an earlier stage, eventually leading to trichogenous state, as compared to the control group. In other words, a hair restoring effect was confirmed. In addition, similar tests were carried out for the fucoidan and a degradation product thereof described in each Example. As a result, similar hair restoring effects could be confirmed.

TABLE 2

| | Duration of Administration (weeks) | | | | | |
| --- | --- | --- | --- | --- | --- | --- |
| | 5 | 6 | 7 | 8 | 9 | 10 |
| | | | Average Score | | | |
| *Kjellmaniella crassifolia*-derived Fucoidan-Administered Group (N = 3) | 0 | 0.3 | 1.7 | 2.0 | 2.3 | 3.0 |
| Control Group (N = 3) | 0 | 0 | 0 | 1.0 | 1.0 | 2.0 |

(3) Male C3H/He mice were purchased from Nippon SLC and used for an experiment from 8 week-old after pre-breeding the mice. The hair on the backside of each mouse was cut with hair clippers, and thereafter shaved with a razor.

Using the fucoidan derived from *Kjellmaniella crassifolia* prepared in item (1) of Example 1, or 7-12SFd-F prepared in item (3) of Example 2, the hair restoring effects were tested in the same manner as in item (2) of Example 13.

The average score in each group was calculated. The results are shown in Table 3.

As shown in Table 3, each of the *Kjellmaniella crassifolia*-derived fucoidan-administered group and the 7-12SFd-F-administered group showed a change in the skin color and an acceleration of hair growth from an earlier stage, eventually leading to trichogenous state, as compared to the control group. Here, when the *Kjellmaniella crassifolia*-derived fucoidan-administered group was compared to the 7-12SFd-F-administered group, the 7-12SFd-F-administered group showed a change in the skin color from a slightly earlier stage. In addition, similar tests were carried out for the fucoidan and a degradation product thereof described in each Example. As a result, similar hair restoring effects could be confirmed.

TABLE 3

| | Duration of Administration (days) | | | | |
| --- | --- | --- | --- | --- | --- |
| | 8 | 9 | 10 | 11 | 12 |
| | | | Average Score | | |
| 7-12SFd-F-Administered Group (N = 8) | 0 | 0.4 | 0.5 | 1.1 | 1.8 |
| *Kjellmaniella crassifolia*-derived Fucoidan-Administered Group (N = 7) | 0 | 0 | 0.4 | 0.7 | 1.3 |
| Control Group (N = 8) | 0 | 0 | 0 | 0.5 | 0.6 |

(4) Male C3H/He mice were purchased from Nippon SLC and used for an experiment from 5 week-old after pre-breeding the mice. 7-12SFd-F prepared in item (3) of Example 2 was suspended and dissolved in ethanol in a concentration of 3%, and the resulting solution was applied onto the backside of the mice in an amount of 200 μL per mouse. To the control group, ethanol was similarly applied. The mice were administered once a day, for 8 consecutive days. Skin was peeled off after the mice were sacrificed by exsanguination on ninth day after the beginning of administration, and the color of the backside skin was analyzed using an image analysis software.

The results are shown in Table 4. The numerical figures in the table are expressed by an average value±standard error of 5 cases, and the asterisk * in the table means that there is a significant difference at a significance level of 5% or less, as compared to the control group. The skin color tone is expressed as the color tone level where white is defined as 0 and black is defined as 100.

In the control group, a state of transition to the telogen was apparently observed, and the skin color became white. On the other hand, the 7-12SFd-F-administered group maintained the anagen, and the skin color was more grayish than that of the control group. It was seen from the above that 7-12SFd-F has a late anagen maintaining action, namely a hair restoring action similar to that in item (1) of Example 13. In addition, similar tests were carried out for the fucoidan and a degradation product thereof described in each Example. As a result, similar hair restoring effects could be confirmed.

TABLE 4

| | Skin Color Tone |
| --- | --- |
| 7-12SFd-F-Administered Group (N = 5) | 24.8 ± 0.61* |
| Control Group (N = 5) | 20.9 ± 1.19 |

Average Value ± Standard Error
*p < 0.05

(5) Male C3H/He mice were purchased from Nippon SLC and used for an experiment from 8 week-old after pre-breeding the mice. The hair on the backside of each mouse was cut with hair clippers, and thereafter shaved with a razor. 7-12SFd-F prepared in item (3) of Example 2 was suspended and dissolved in ethanol in a concentration of 3%, and the resulting solution was applied onto the above-mentioned hair-cut site of the backside of the mice in an amount of 200 μL per mouse. To the control group, ethanol was similarly applied. The mice were administered once a day, for consecutive days. The area where the trichogenous state was observed was determined on the twenty-first day from the day of the beginning of administration (the day following the shaving), and expressed as the ratio (%) to the shaved area.

The results are shown in Table 5. The numerical figures in the table are expressed by an average value±standard error of 7 to 8 cases.

As compared to the control group, transition from the telogen to the anagen was clearly accelerated, the 7-12SFd-F-administered group led to a trichogenous state in a higher proportion. In addition, similar tests were carried out for the fucoidan and a degradation product thereof described in each Example. As a result, similar hair restoring effects could be confirmed.

TABLE 5

| | Trichogenous Ratio (%) (Trichogenous Area/Shaved Area) |
| --- | --- |
| 7-12SFd-F-Administered Group (N = 7) | 31.8 ± 12.8 |
| Control Group (N = 8) | 12.0 ± 4.17 |

Average Value ± Standard Error (6) Using the fucoidan derived from *Kjellmaniella crassifolia* prepared in item (1) of Example 1, and F-rich fucoidan prepared in item (2) of Example 16 described below, the hair restoring effect was confirmed in the same manner as in item (5) of Example 13. The results are shown in Table 6. As compared to the control group, higher ratios of the animals were led to trichogenous state in the fucoidan-administered group and the F-rich fucoidan-administered group.

TABLE 6

|  | Trichogenous Ratio (%) (Trichogenous Area/ Shaved Area) |
|---|---|
| Fucoidan-Administered Group (N = 6) | 44.4 ± 10.6 |
| F-rich Fucoidan (N = 6) | 45.6 ± 9.6 |
| Control Group (N = 6) | 26.7 ± 7.5 |

Average Value ± Standard Error (7) Male C3H/He mice were purchased from Nippon SLC and used for an experiment from 8 week-old after pre-breeding the mice. The hair on the backside of each mouse was cut with hair clippers, and thereafter shaved with a razor. 7-12SFd-F prepared in item (3) of Example 2 was suspended and dissolved in ethanol in a concentration of 3%, and the resulting solution was applied onto the above hair-cut site of the backside of the mice in an amount of 200 µL per mouse. To the control group, ethanol was similarly applied. The mice were administered once a day, for consecutive days. Skin on the backside was peeled off after the mice were sacrificed by exsanguination on the twenty-first day from the day of the beginning of administration (the day following the shaving), and homogenized, to prepare an extract. The glucose-6-phosphate dehydrogenase activity (G-6-PDH activity) in the extract of skin on the backside was assayed using a test kit manufactured by ROCHE DIAGNOSTICS GmbH, and the alkaline phosphatase activity (ALP activity) was assayed using a test kit manufactured by Wako Pure Chemical Industries, Ltd. Incidentally, the enzyme activities of G-6-PDH and ALP are known to be increased in the tissues in which a hair restoring effect is observed.

The results are shown in Table 7. The numerical figures in the table are expressed by an average value±standard error of 7 to 8 cases. It is clearly shown in the 7-12SFd-F-administered group that the enzyme activities were increased in the skin tissues, and that transition from the telogen to the anagen was promoted, as compared to the control group. Namely, a hair restoring effect was confirmed. In addition, similar tests were carried out for the fucoidan and a degradation product thereof described in each Example. As a result, similar hair restoring effects could be confirmed.

TABLE 7

|  | G-6-PDH Activity (IU/g tissue) | ALP Activity (IU/g tissue) |
|---|---|---|
| 7-12SFd-F-Administered Group (N = 7) | 1.22 ± 0.26 | 0.35 ± 0.08 |
| Control Group (N = 8) | 0.84 ± 0.18 | 0.22 ± 0.06 |

Average Value ± Standard Error (8) Twenty-five adult women of ages 20- to 35-years old were subjected to a blind functional test in which the lotion containing the fucoidan derived from *Kjellmaniella crassifolia* of the present invention described in item (1) of Example 5 was compared with the control lotion containing no fucoidan. As a result, the number of persons who judged "more effective" is shown in Table 8.

TABLE 8

|  | Moistness of Skin | Smoothness on Skin | Liveliness of Skin |
|---|---|---|---|
| Lotion of Present Invention | 21 | 19 | 16 |
| Control Lotion | 5 | 6 | 9 |

It is shown from the above results that the lotion containing the fucoidan of the present invention show excellent examination results in all of items of moistness, smoothness and liveliness of skin, showing that the lotion has a skin cosmeticizing action.

In addition, similar tests were carried out for each of a lotion containing the other fucoidans and a degradation product thereof. As a result, similar skin cosmeticizing effects could be confirmed.

(9) Fifty milliliters of a refreshing drink containing 200 mg of the fucoidan derived from *Kjellmaniella crassifolia* described in item (1) of Example 1 (3% malt sugar solution; 0.05% ume powder; 0.2% ⅕ clear lemon juice; and 0.02% citric anhydride) was prepared, and the skin cosmeticizing effect of this drink was studied. After drinking one drink every day for 3 months, pruritis of the skin and pruritis of the eyes were suppressed, and reduction in blotches was confirmed. Also, an increase in the hair and suppression of turning to silver hair were observed. Further, dry skin was ameliorated.

In addition, similar tests were carried out for each of a drink containing the other fucoidans and a degradation product thereof. As a result, similar skin cosmeticizing effects and hair restoring effects were confirmed.

(10) Using the fucoidan derived from *Kjellmaniella crassifolia* described in item (1) of Example 1, the milky lotion having the following composition was prepared. Here, "part(s)" represents part(s) by weight.

| Liquid paraffin | 23.0 parts |
|---|---|
| Isopropyl myristate | 5.0 parts |
| Vaseline | 6.0 parts |
| Bees wax | 5.0 parts |
| Stearic acid | 2.0 parts |
| Behenyl alcohol | 1.0 part |
| Sorbitan monostearate | 3.0 parts |
| Polyoxyethylene(20) sorbitan monostearate | 3.0 parts |
| 1,3-Butylene glycol | 3.0 parts |
| Paraben | 0.3 parts |
| Fucoidan | 1.0 part |
| Perfume | Appropriate Amount |
| Purified water | Balance |

Six persons with sensitive skin used the above milky lotion twice a day, in the morning and in the evening, every day for 3 months. As a result, the skin conditions were ameliorated in all members, without developing undesired events such as inflammation at all.

Example 14

(1) Two-hundred milligrams (1.1 mmol) of D-(+)-glucose was dissolved in 10 mL of pyridine, and 1.05 g (6.6 mmol) of Pyridine Sulfur Trioxide Complex (Pyr.SO$_3$: manufactured by Tokyo Kasei) was added thereto at room temperature. Thereafter, the resulting mixture was stirred at room temperature for several minutes and further stirred at 60° C. for 1 hour. The reaction solution was diluted with water, and the pH of the solution was adjusted to near neutrality with an aqueous saturated barium hydroxide solution, and the resulting solution was then dried under reduced pressure. Water was again added to the resulting concentrate, and the resulting solution was again dried under reduced pressure. These steps were repeated one more time. A small amount of water was added to the resulting concentrate, and precipitates of barium sulfate were removed by centrifugation. The resulting supernatant was applied onto a cationic exchange column [Amberlite IRA-120 ($Na^+$) (Organo)]. Finally, the resulting column-effluent fractions were concentrated under reduced pressure, to give 700 mg of sulfated (—$SO_3$—$Na^+$) D-(+)-glucose. Also, sulfated fucose, sulfated mannose, sulfated galactose, sulfated xylose, sulfated 2-deoxy-glucose, and sulfated talose were similarly prepared.

(2) The hair restoring effect of the sulfated glucose prepared in item (1) of Example 14 was studied in the same manner as in item (3) of Example 13. Here, the sulfated glucose was dissolved in 50% ethanol in a concentration of 3%, and the resulting solution was applied onto the backside of the mice once a day in an amount of 200 μL per mouse. To the control group, 50% ethanol alone was applied. As a result, as shown in Table 9, the sulfated glucose-administered group showed a change in the skin color and an acceleration of hair growth was from an earlier stage, eventually leading to trichogenous state, as compared to the control group. In addition, similar tests were carried out for the sulfated fucose, the sulfated mannose, the sulfated galactose, the sulfated xylose, the sulfated 2-deoxy-glucose and the sulfated talose. As a result, similar hair restoring effects were confirmed.

TABLE 9

| | Duration of Administration (days) | | | | |
| --- | --- | --- | --- | --- | --- |
| | 11 | 12 | 13 | 14 | 15 |
| | Average Score | | | | |
| Sulfated Glucose-Administered Group (N = 5) | 0.6 | 0.6 | 1.0 | 1.6 | 1.8 |
| Control Group (N = 5) | 0.2 | 0.4 | 0.6 | 0.8 | 1.0 |

Example 15

(1) Two day-old male C3H/He mice were purchased from Nippon SLC together with the mother mice and used for an experiment from 5 day-old. The mice were sacrificed by exsanguination, and the whiskers together with the subcutaneous tissues were collected using scissors and tweezers. Further, the whiskers with the hair follicles were separated in a petri dish under the microscope according to the method by Ogawa et al. (*J. Invest. Dermatol* 103: 306-309, 1994). Fourteen to sixteen whiskers were collected from the right and left sides per mouse.

The fucoidan derived from *Kjellmaniella crassifolia* described in item (1) of Example 1, and 7-12SFd-F described in item (3) of Example 2 were dissolved in an RPMI-1640 medium to prepare a solution having a 20-fold concentration of the given concentration, and a ¹⁄₂₀-fold amount of the solution was added to the culture system. The same amount of the medium was added to the control group. Here, the given concentrations of each sample added are respectively expressed as the concentration per mL medium (mg/mL) in Table 10. For the culture of the whiskers, tissue culture dishes Falcon 3037 (manufactured by Becton Dickinson Labware) were used, and 0.7 mL of an RPMI-1640 medium supplemented with 20% FCS was placed in the central wells, and a sterilized stainless mesh (manufactured by Ikeda Rika K.K.) and lens paper (manufactured by T.C. Case K.K.) were placed over the wells. The whiskers were put on the paper and cultured. The fucoidan derived from *Kjellmaniella crassifolia* and 7-12SFd-F were previously added to the medium. The culture was carried out at 35° C. for 6 days in the presence of 5% $CO_2$. The length of whisker was determined to the order of 0.1 mm before the beginning and after the termination of the culture under the microscope using a caliper. Three to five whiskers were used for the determination per group of each of the sample concentrations, and the length of grown whisker was indicated by an average value±standard error. In addition, Student's t-test was used for test of significance, and P value was determined against the control group. The results are shown in Table 10.

TABLE 10

| Added Sample | Concentration (mg/mL) | Number of Animals | Length of Grown Whisker (mm) (Average Value ± Standard Error) | P Value |
| --- | --- | --- | --- | --- |
| 7-12SFd-F | 0.01 | 3 | 1.33 ± 0.88 | 0.58 |
| | 0.1 | 3 | 1.67 ± 0.88 | 0.38 |
| | 1 | 4 | 2.75 ± 0.63 | 0.04 |
| *Kjellmaniella crassifolia*-derived Fucoidan | 0.1 | 4 | 1.25 ± 0.95 | 0.67 |
| | 1 | 4 | 2.50 ± 0.50 | 0.05 |
| Control | 0 | 5 | 0.80 ± 0.49 | — |

As a result, the whiskers of mice were grown in the cases of the fucoidan derived from *Kjellmaniella crassifolia* and 7-12SFd-F in a concentration-dependent manner as compared to those of the control. In other words, it could be confirmed that the fucoidan derived from *Kjellmaniella crassifolia* and 7-12SFd-F had hair restoring effects. In addition, similar tests were carried out for the fucoidan and a degradation product thereof described in each Example. As a result, similar hair restoring effects could be confirmed.

(2) Two day-old male C3H/He mice were purchased from Nippon SLC together with the mother mice and used for an experiment from 9 day-old. The hair restoring effects for the fucoidan derived from *Kjellmaniella crassifolia* described in item (1) of Example 1 and 7-12SFd-F described in item (3) of Example 2 were evaluated in the same manner as in item (1) of Example 15. The results are shown in Table 11.

TABLE 11

| Added Sample | Concentration (mg/mL) | Number of Animals | Length of Grown Whisker (mm) (Average Value ± Standard Error) | P Value |
| --- | --- | --- | --- | --- |
| 7-12SFd-F | 0.001 | 5 | 0.34 ± 0.10 | 0.12 |
| | 0.01 | 5 | 0.66 ± 0.16 | 0.02 |
| | 0.1 | 5 | 0.51 ± 0.10 | 0.01 |
| *Kjellmaniella crassifolia*-derived Fucoidan | 0.01 | 5 | 0.62 ± 0.17 | 0.03 |
| | 0.1 | 5 | 0.80 ± 0.17 | 0.01 |
| Control | 0 | 5 | 0.10 ± 0.10 | — |

As a result, in the case where the whiskers of 9 day-old mice were used, the whiskers of mice were also grown significantly in the cases of the fucoidan derived from *Kjellmaniella crassifolia* and 7-12SFd-F, as compared to those of the control. In other words, it could be confirmed that the fucoidan derived from 10 *Kjellmaniella crassifolia* and 7-12SFd-F had hair restoring effects. In addition, similar tests were carried out for the fucoidan and a degradation product thereof described in each Example. As a result, similar hair restoring effects could be confirmed.

Example 16

(1) Thirty grams of the fucoidan derived from *Kjellmaniella crassifolia* described in item (1) of Example 1 was suspended in 12 liters of distilled water at room temperature with stirring for 30 minutes. This suspension was centrifuged at 10000×g for 40 minutes, and its supernatant was collected. This supernatant was subjected to sterile filtration with a membrane filter (0.22 µm) (manufactured by Millipore Corporation), to give 21.4 g of a lyophilized product. The resulting product was referred to as TaKaRa Kombu Fucoidan Bf (hereinafter referred to "Fucoidan Bf").

(2) Five-hundred grams of dried *Kjellmaniella crassifolia* was cut into thin pieces, and washed with 10 L of 80% ethanol. Thereafter, the resulting product was stirred at 25° C. for 3 days in 50 liters of 10% ethanol containing 1 mM potassium chloride, and filtered with a stainless screen having a screen diameter of 32 µm, to give about 45 liters of a filtrate. Thirty-four liters of this filtrate was heated at 80° C. for 3 hours, and thereafter cooled to 50° C. The resulting solution was concentrated with an ultrafilter OMEGA Cassette (manufactured by Filtron) having an excluding molecular weight of 10000, with keeping the liquid temperature at 50° C. Further, the concentrate was desalted with 5 liters of distilled water heated to 50° C., and the flow path was washed twice by adding 200 mL of the same distilled water, and washings were collected, to give 1.5 liters of a concentrate. This concentrate was lyophilized, to give 8.2 g of F-rich fucoidan.

(3) Two day-old male C3H/He mice were purchased from Nippon SLC together with the mother mice and used for an experiment from 14 day-old. The hair restoring effects for Fucoidan Bf described in item (1) of Example 16 and F-rich fucoidan described in item (2) of Example 16 were evaluated in the same manner as in item (1) of Example 15. The length of whisker was determined to the order of 0.1 mm before the beginning and after the termination of the culture under the microscope using a caliper, and the length of grown whisker was indicated by an average value±standard error. In addition, Student's t-test was used for test of significance, and P value was determined against the control group. The results are shown in Table 12.

TABLE 12

| Added Sample | Concentration (mg/mL) | Number of Animals | Length of Grown Whisker (mm) (Average Value ± Standard Error) | P Value |
|---|---|---|---|---|
| Fucoidan Bf | 0.01 | 6 | 0.62 ± 0.18 | 0.03 |
|  | 0.1 | 6 | 0.82 ± 0.18 | 0.01 |
| F-rich Fucoidan | 0.01 | 6 | 0.68 ± 0.22 | 0.03 |
|  | 0.1 | 6 | 0.65 ± 0.12 | 0.01 |
| Control | 0 | 6 | 0.10 ± 0.10 | — |

As a result, the whiskers of mice were grown significantly in the cases of Fucoidan Bf and F-rich fucoidan as compared to those of the control. In other words, it could be confirmed that they had hair restoring effects. In addition, similar tests were carried out for the fucoidan and a degradation product thereof described in each Example. As a result, similar hair restoring effects could be confirmed.

Example 17

Two day-old male C3H/He mice were purchased from Nippon SLC together with the mother mice and used for an experiment from 5 day-old. The hair restoring effects for F-rich fucoidan described in item (2) of Example 16, the fucoidan derived from sporophyll of *Undaria pinnatifida* described in Example 6, the fucoidan derived from *Fucus vesiculosus* described in Example 7, the fucoidan derived from Nemacystus decipiens described in Example 9, and the fucoidan derived from *Cladosiphon okamuranus* described in Example 12 were evaluated in the same manner as in item (1) of Example 15. The results are shown in Table 13.

TABLE 13

| Added Sample | Concentration (mg/mL) | Number of Animals | Length of Grown Whisker (mm) (Average Value ± Standard Error) | P Value |
|---|---|---|---|---|
| F-rich Fucoidan | 0.01 | 5 | 1.72 ± 0.42 | 0.02 |
| Sporophyll of *Undaria pinnatifida*-derived Fucoidan | 0.01 | 5 | 0.62 ± 0.30 | 0.54 |
| *Fucus vesiculosus*-derived Fucoidan | 0.01 | 5 | 1.40 ± 0.38 | 0.04 |
| *Nemacystus decipiens*-derived Fucoidan | 0.01 | 5 | 0.74 ± 0.24 | 0.31 |
| *Cladosiphon okamuranus*-derived Fucoidan | 0.01 | 5 | 0.90 ± 0.25 | 0.17 |
| Control | 0 | 6 | 0.38 ± 0.23 | — |

As a result, the whiskers of mice were grown significantly in the cases of these fucoidans as compared to those of the control. In addition, the whiskers of mice were especially well grown in the cases of F-rich fucoidan and the fucoidan derived from *Fucus vesiculosus*. In other words, it could be confirmed that the action for the growth of the whiskers of mouse may be strong or weak depending on the kinds of fucoidans, and that there are stronger hair restoring effects in F-rich fucoidan derived from *Kjellmaniella crassifolia* and the fucoidan derived from *Fucus vesiculosus*, as compared to those of other ones. In addition, similar tests were carried out for the fucoidan and a degradation product thereof described in each Example. As a result, hair restoring effects could be confirmed.

Example 18

Two day-old male C3H/He mice were purchased from Nippon SLC together with the mother mice and used for an experiment from 6 day-old. The hair restoring effect for the sulfated glucose described in item (1) of Example 14 was evaluated in the same manner as in item (1) of Example 15. The results are shown in Table 14.

TABLE 14

| Added Sample | Concentration (mg/mL) | Number of Animals | Length of Grown Whisker (mm) (Average Value ± Standard Error) | P Value |
|---|---|---|---|---|
| Sulfated Glucose | 0.1 | 9 | 0.39 ± 0.11 | 0.890 |
| | 1 | 8 | 1.31 ± 0.31 | 0.004 |
| Control | 0 | 18 | 0.42 ± 0.13 | — |

As a result, the whiskers of mice were grown significantly in the case of 1 mg/mL sulfated glucose, as compared to those of the control. In other words, it could be confirmed that the sulfated glucose also had a hair restoring effect in this experimental system. In addition, it could be confirmed that each of the sulfated monosaccharides described in Example 14 also had a similar effect.

Example 19

Male C3H/He mice were purchased from Nippon SLC and used for an experiment from 8 week-old after pre-breeding the mice. The hair on the backside of each mouse was cut with hair clippers, and thereafter shaved with a razor. Fucoidan Bf described in item (1) of Example 16 alone, or Fucoidan Bf and carpronium chloride or minoxidil, which is an effective ingredient of a commercially available hair-care product, were dissolved in 30% ethanol solution so as to have a concentration as shown in Table 15, to give each ethanol solution. The resulting ethanol solution was applied onto the above hair-cut site of the backside of the mice in an amount of 200 μL per mouse. To the control group, 30% ethanol solution was similarly applied. The mice were administered once a day, for consecutive days. The administered sites were observed over the passage of time from the day of the beginning of administration (the day following the shaving), and the trichogenous area was determined on the twenty-first day after shaving and expressed as the ratio (%) to the shaved area. The average value±standard error of 6 cases for each group are shown in Table 15.

No hair restoring effect by administration by the application of carpronium chloride which is an effective ingredient of a commercially available hair-care product A was found in this experimental system. Therefore, there was no difference with the control group. However, the Fucoidan Bf/carpronium chloride-combined administration group showed a change in the skin color was observed from an earlier stage, eventually leading to trichogenous state. The trichogenous ratio was also higher than that of the control group. Individuals showing a trichogenous ratio of 60% or more were not found in the control group and in the carpronium chloride-administered group, whereas such individuals were found in 3 out of 6 cases in the Fucoidan Bf/carpronium chloride-combined administration group.

On the other hand, a hair restoring effect was found by applying an effective ingredient of a commercially available hair-care product B, minoxidil, at a concentration of 1%. It was observed that the skin was changed in the color from an earlier stage, eventually led to trichogenous state. The effect was weak at a concentration of 0.1%. Further, in the Fucoidan Bf/minoxidil-combined administration group, there was found a tendency to enhance a hair restoring effect. Specifically, the individuals showing a trichogenous ratio of 60% or more at the termination of the experiment were found in 4 out of 6 cases in the 1% minoxidil-administered group, whereas all 6 cases showed trichogenous state well in the Fucoidan Bf/minoxidil-combined administration group. On the other hand, in the 0.1% minoxidil-administered group in which the effect was weak, those individuals were found only in 1 out of 6 cases, whereas those individuals were found in 3 out of 6 cases in the Fucoidan Bf/minoxidil-combined administration group.

It is seen from the above that the hair restoring effect was synergically enhanced by using Fucoidan Bf together with minoxidil or carpronium chloride. In addition, similar tests were carried out for each of the other fucoidans, fucoidan degradation products, the sulfated monosaccharides and the like. As a result, similar results were obtained.

TABLE 15

| Concentration of Added Sample | Trichogenous Ratio (%) (Trichogenous Area/ Shaved Area) | Number of Individuals with Trichogenous Ratio of 60% or More |
|---|---|---|
| 0.5% Carpronium Chloride | 23.9 ± 4.9 | 0/6 |
| 0.5% Carpronium Chloride + 3% Fucoidan Bf | 55.4 ± 11.1 | 3/6 |
| 1% Minoxidil | 69.1 ± 13.9 | 4/6 |
| 1% Minoxidil + 3% Fucoidan Bf | 92.2 ± 2.5 | 6/6 |
| 0.1% Minoxidil | 42.9 ± 5.5 | 1/6 |
| 0.1% Minoxidil + 3% Fucoidan Bf | 48.2 ± 10.0 | 3/6 |
| Control Group | 29.2 ± 9.2 | 0/6 |

Average Value ± Standard Error

Example 20

Male C3H/He mice were purchased from Nippon SLC and used for an experiment from 8 week-old after pre-breeding the mice. The hair on the backside of each mouse was cut with hair clippers, and thereafter shaved with a razor. Fucoidan Bf described in item (1) of Example 16 was mixed with an ointment base [hydrophilic ointment (manufactured by Maruishi Pharmaceutical Co., Ltd.)] so as to have a concentration of 3%, and the resulting ointment (fucoidan ointment) was applied onto the above hair-cut site of the backside of the mice in an amount of 0.2 g per mouse. To the control group, the ointment base alone was similarly applied. The mice were administered once a day, for consecutive days. The administered sites were observed over the passage of time from the day of the beginning of administration (the day following the shaving), and a change in the skin color tone was determined by scoring. Specifically, the scoring criteria were defined as follows: Score 0: no change, Score 1: the skin color being changed to blue, Score 2: the skin color being changed to black-blue to gray, Score 3: trichogenous state being observed, Score 4: the state before the shaving being almost restored. The score for each group is expressed by an average value±standard error of 6 cases in Table 16. In addition, the trichogenous area was determined on the twenty-first day after shaving and expressed as the ratio (%) to the shaved area. Student's t-test was used for test of significance, and P value was determined against the control group. The results are shown in Table 17. Here, the trichogenous ratio in the table is expressed by an average value±standard error of 6 cases in each group.

As a result, a marked hair restoring effect was found by applying the fucoidan ointment. A change in the skin color was observed from an earlier stage as compared to the control group, eventually leading to trichogenous state. Also, at the termination of the experiment, the state before the shaving was almost restored in all cases. In addition, ointments were similarly prepared using the fucoidan and a degradation product thereof described in each Example, and similar tests were carried out. As a result, similar hair restoring effects could be confirmed.

TABLE 16

| | Days After Shaving | | | | | | |
|---|---|---|---|---|---|---|---|
| | 9 | 10 | 11 | 12 | 13 | 14 | 15 |
| | Score (Average Value ± Standard Error) | | | | | | |
| Fucoidan Ointment Group (N = 6) | 0.0 ± 0.0 | 0.7 ± 0.2 | 1.0 ± 0.0 | 1.5 ± 0.2 | 2.0 ± 0.0 | 2.7 ± 0.2 | 3.0 ± 0.0 |
| Control Group (N = 6) | 0.0 ± 0.0 | 0.2 ± 0.2 | 0.4 ± 0.2 | 1.2 ± 0.2 | 1.6 ±± 0.2 | 1.8 ± 0.4 | 2.4 ± 0.0 |

Average Value ± Standard Error

TABLE 17

| | Trichogenous Ratio (%) (Trichogenous Area/Shaved Area) | P Value |
|---|---|---|
| Fucoidan Ointment Group (N = 6) | 95.4 ± 2.9 | P < 0.0001 |
| Control Group (N = 6) | 31.3 ± 5.7 | — |

Average Value ± Standard Error

Deposited Biological Materials (1) Name and Addressee of Depository Authority
the Ministry of International Trade and Industry, National Institute of Bioscience and Human-Technology, Agency of Industrial Science and Technology
1-3, Higashi 1 chome, Tsukuba-shi, Ibaraki-ken, Japan (Zip code 305)

(2) Deposited Microorganisms
(i) *Alteromonas* sp. SN-1009
Original Date of Deposit: Feb. 13, 1996
Date of Request for Transfer to International Deposit: Nov. 15, 1996
Accession Number: FERM BP-5747
(ii) *Flavobacterium* sp. SA-0082
Original Date of Deposit: Mar. 29, 1995
Date of Request for Transfer to International Deposit: Feb. 15, 1996
Accession Number: FERM BP-5402

INDUSTRIAL APPLICABILITY

According to the present invention, there are provided biocosmetics, comprising as an effective ingredient a compound selected from a fucoidan or a degradation product thereof, a sulfated monosaccharide, or a salt thereof, wherein the biocosmetics are highly safe. In addition, there are provided cosmetics which can be used as foods or beverages for cosmeticizing skin and for restoring hair, comprising as an effective ingredient a compound selected from a fucoidan or a degradation product thereof, a sulfated monosaccharide, or a salt thereof, and these foods or beverages are useful as functional foods or beverages having skin cosmeticizing action and/or hair restoring action. Especially a beverage comprising as an effective ingredient a compound selected from a fucoidan, a degradation product thereof, a sulfated monosaccharide, or a salt thereof can be taken daily as cosmetics or hair-care products for drinking, so that the beverage is extremely useful in maintenance of good skin condition, inhibition of skin aging, prophylaxis of skin aging, maintenance of hair, hair nourishment, increase in hair, and the like.

In addition, by using the above-mentioned effective ingredient used in the present invention together with the effective ingredient of the conventional hair-care product (hair restoring action-enhancing component), the hair restoring action can be synergistically enhanced. Therefore, according to the present invention, there is provided a hair-care product having very excellent hair restoring action as compared to those of the conventional ones, comprising the above-mentioned effective ingredient and the hair restoring action-enhancing component.

The invention claimed is:

1. A method of restoring hair, the method comprising applying or pasting a composition to a site in need of restoring hair, said composition comprising:
as an effective ingredient a compound selected from the group consisting of a fucoidan and a degradation product of said fucoidan; and
a hair restoring action-enhancing component selected from the group consisting of minoxidil, calpronium chloride and mixtures thereof;
wherein said degradation product is a compound represented by the following formula (V), (VI) or (VII):

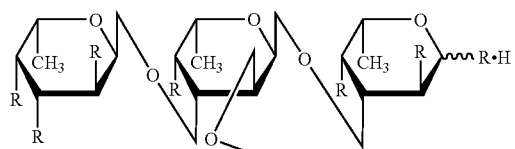
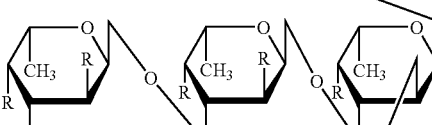
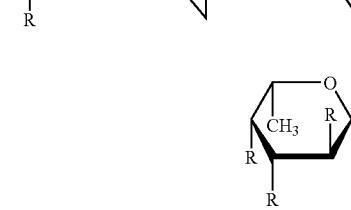

wherein R is OH or $OSO_3H$ to make the sulfated saccharide;

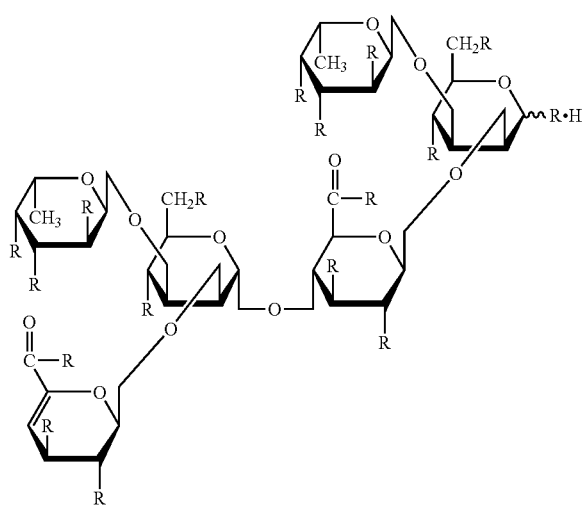
(VI)
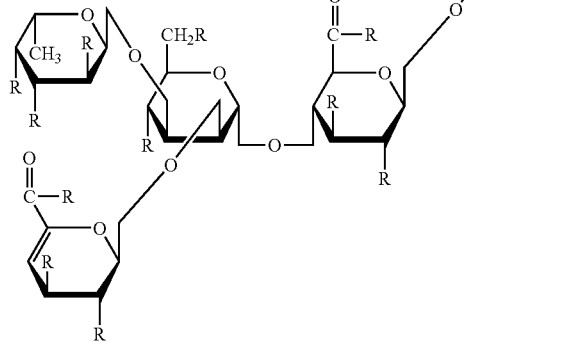
wherein R is OH or OSO$_3$H to make the sulfated saccharide; or
(VII)
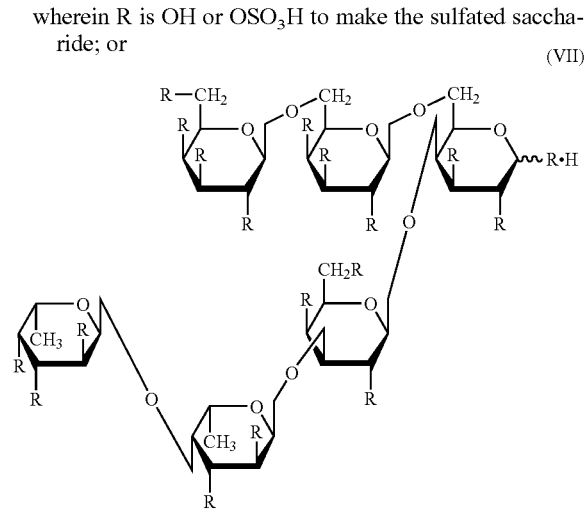
wherein R is OH or OSO$_3$H to make the sulfated saccharide.
2. The method according to claim 1, wherein the fucoidan comprises a sulfated saccharide represented by the following general formula:
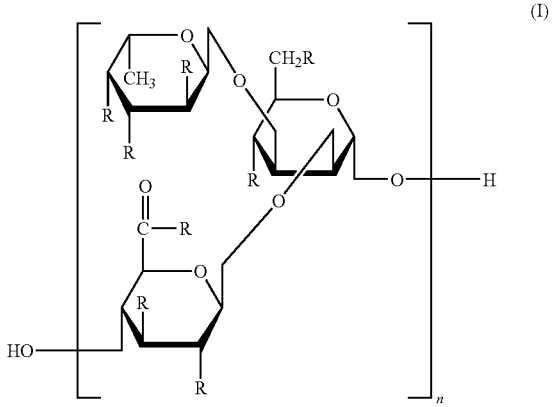
(I)
wherein R is OH or OSO$_3$H to make the sulfated saccharide and n is an integer of 1 to 5;
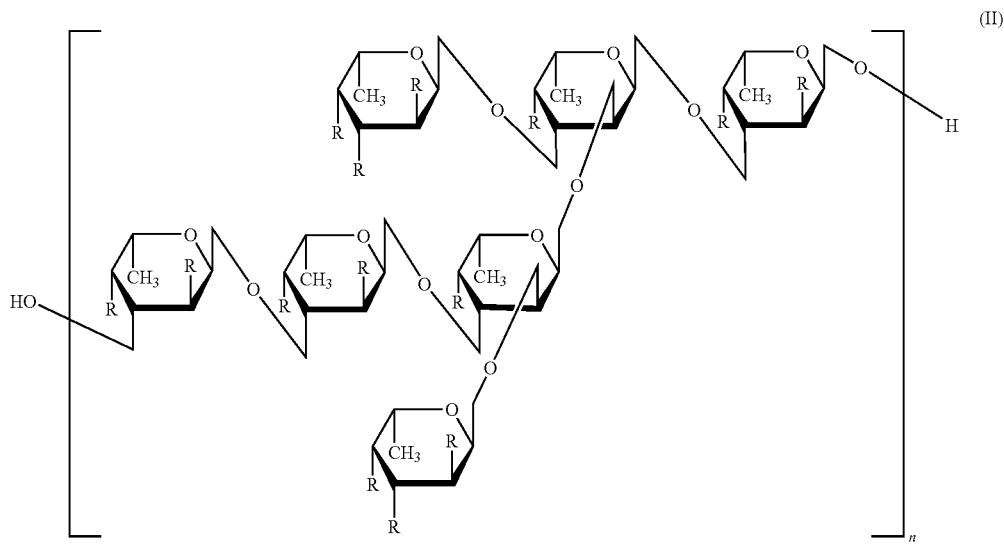
(II)

wherein R is OH or OSO$_3$H to make the sulfated saccharide, and n is an integer of 1 to 5; or

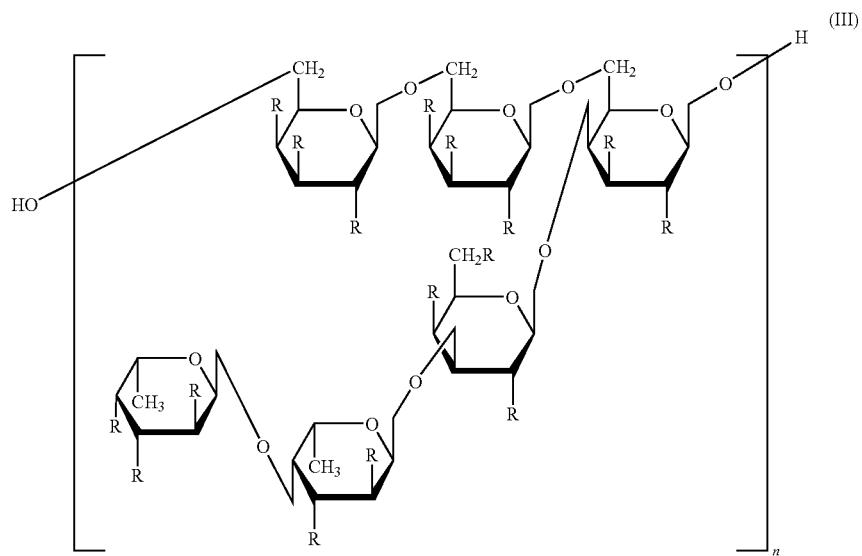

wherein R is OH or OSO$_3$H to make the sulfated saccharide, and n is an integer of 1 to 5.

3. The method according to claim 1, wherein the fucoidan is a non-stringy fucoidan.

4. The method according to claim 1, 2, or 3, wherein the composition is a lotion, a milky lotion, a cream, an ointment, a hair lotion, a hair tonic, a hair nourishing agent, a hair loss preventing agent, or a shampoo agent.

* * * * *